US011011265B2

(12) United States Patent
Madabhushi et al.

(10) Patent No.: US 11,011,265 B2
(45) Date of Patent: May 18, 2021

(54) PREDICTING PROSTATE CANCER RISK O PROGRESSION WITH MULTIPARAMETRIC MAGNETIC RESONANCE IMAGING USING MACHINE LEARNING AND PERITUMORAL RADIOMICS

(71) Applicant: Case Western Reserve University, Cleveland, OH (US)

(72) Inventors: Anant Madabhushi, Shaker Heights, OH (US); Ahmad Algohary, Shaker Heights, OH (US); Rakesh Shiradkar, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 104 days.

(21) Appl. No.: 16/395,904

(22) Filed: Apr. 26, 2019

(65) Prior Publication Data

US 2020/0005931 A1     Jan. 2, 2020

Related U.S. Application Data

(60) Provisional application No. 62/691,090, filed on Jun. 28, 2018.

(51) Int. Cl.
*G16H 30/40* (2018.01)
*G06T 7/00* (2017.01)
(Continued)

(52) U.S. Cl.
CPC ............ *G16H 30/40* (2018.01); *A61B 5/055* (2013.01); *A61B 5/4381* (2013.01);
(Continued)

(58) Field of Classification Search
CPC ........ G16H 30/40; G16H 50/20; G16H 50/30; G16H 50/70; G06T 7/11; G06T 7/0012; G06T 2207/30096; G06T 2207/20081; G06T 2207/30081; G06T 2207/10088; A61B 5/055; A61B 5/4381; A61B 5/7267;
(Continued)

(56) References Cited

U.S. PATENT DOCUMENTS 9,779,213 B2 * 10/2017 Donovan ............... G16H 50/50
10,489,908 B2 * 11/2019 Kiraly ................... G06T 7/0012
(Continued)

OTHER PUBLICATIONS

U.S. Appl. No. 16/395,922, filed Apr. 26, 2019.
Non Final Office Action dated Oct. 16, 2020 in connection with U.S. Appl. No. 16/395,922.

*Primary Examiner* — Juan A Torres
(74) *Attorney, Agent, or Firm* — Eschweiler & Potashnik, LLC

(57) ABSTRACT

Embodiments facilitate stratification of a patient according to prostate cancer (PCa) risk. A first set of embodiments relates to training of a machine learning classifier to compute a probability that a patient has a low-risk of PCa progression based on intratumoral radiomic features and peritumoral radiomic features extracted from multi-parametric magnetic resonance imaging (mpMRI) images. A second set of embodiments relates to classifying a patient as low-risk of PCa progression, or high-risk of PCa progression, based on radiomic features extracted from mpMRI imagery of the patient.

23 Claims, 20 Drawing Sheets

(51) Int. Cl.
*G06T 7/11* (2017.01)
*G16H 50/20* (2018.01)
*A61B 5/055* (2006.01)
*A61B 5/00* (2006.01)
*A61N 5/10* (2006.01)
*G06K 9/62* (2006.01)
*G16H 50/30* (2018.01)

(52) U.S. Cl.
CPC .......... *A61B 5/7267* (2013.01); *A61B 5/7275* (2013.01); *A61B 5/7425* (2013.01); *A61N 5/1039* (2013.01); *G06K 9/628* (2013.01); *G06K 9/6228* (2013.01); *G06K 9/6256* (2013.01); *G06K 9/6261* (2013.01); *G06T 7/0012* (2013.01); *G06T 7/11* (2017.01); *G16H 50/20* (2018.01); *G06K 2209/053* (2013.01); *G06T 2207/10088* (2013.01); *G06T 2207/20081* (2013.01); *G06T 2207/30081* (2013.01); *G06T 2207/30096* (2013.01); *G16H 50/30* (2018.01)

(58) Field of Classification Search
CPC ................ A61B 5/7275; A61B 5/7425; A61B 2576/026; A61B 5/4842; A61B 5/742; G06K 9/6228; G06K 9/6256; G06K 9/6261; G06K 9/628; G06K 2209/053; G06K 9/6273; G01R 33/5608
USPC .......................................................... 382/128
See application file for complete search history.

(56) References Cited

U.S. PATENT DOCUMENTS

| | | | |
|---|---|---|---|
| 2015/0176072 A1* | 6/2015 | Wang | C12Q 1/6883 506/9 |
| 2015/0356730 A1* | 12/2015 | Grove | G06T 7/64 382/124 |
| 2015/0368724 A1 | 12/2015 | Aharonov | |
| 2017/0035381 A1* | 2/2017 | Madabhushi | A61B 6/5217 |
| 2017/0039737 A1* | 2/2017 | Madabhushi | A61B 5/08 |
| 2018/0240233 A1* | 8/2018 | Kiraly | G06T 7/0012 |
| 2019/0087532 A1* | 3/2019 | Madabhushi | G06K 9/4628 |
| 2019/0159745 A1* | 5/2019 | Madabhushi | G06K 9/46 |
| 2019/0287243 A1* | 9/2019 | Madabhushi | G06K 9/6286 |
| 2019/0347789 A1* | 11/2019 | Vaidya | G06K 9/0014 |
| 2019/0357870 A1* | 11/2019 | Madabhushi | G06N 20/00 |
| 2020/0063215 A1* | 2/2020 | Permuth | C12Q 1/6886 |

* cited by examiner

| Cohort | Institution 1 | Institution 2 | Institution 3 | Institution 4 |
|---|---|---|---|---|
| Number of Subjects | 32 | 44 | 134 | 81 |
| Age (mean ± SD) | 65.1 ± 6.4 | 62.6 ± 10.8 | 64.3 ± 5.6 | 68.5 ± 8.05 |
| PSA (mean ± SD) ng/ml | 6.9 ± 5.8 | 5.9 ± 4.2 | 9.8 ± 6.3 | 8.08 ± 6.1 |
| Lesion size (mean ± SD) cm³ | 1.10 ± 1.79 | 0.67 ± 0.82 | 1.02 ± 1.16 | 0.86 ± 0.66 |
| Gleason Score (mean ± SD) | 7.41 ± 1.02 | 7.83 ± 1.29 | 7.62 ± 1.66 | 6.84 ± 0.95 |
| PIRADS (mean ± SD) | 4.19 ± 1.05 | 3.65 ± 1.06 | 3.59 ± 1.35 | 2.56 ± 1.59 |
| Scanner | | | | |
| Brand | Philips Achieva | Siemens Verio | Siemens Verio | Philips Achieva |
| Coil type | Body coil | Endorectal coil | Body coil | Endorectal coil |
| T2-weighted MRI | | | | |
| Field-of-view (mm²) | 220 x 220 | 140 x 140 | 200 x 200 | 260 x 260 |
| Matrix size | 444 x 332 | 384 x 384 | 320 x 320 | 256 x 256 |
| Diffusion-Weighted MRI | | | | |
| Field-of-view (mm²) | 180 x 180 | 260 x 186 | 260 x 260 | 260 x 260 |
| Matrix size | 128 x 128 | 116 x 162 | 128 x 128 | 128 x 128 |
| b-values (s/mm²) | 0, 1500 | 0, 2000 | 0, 100, 200, 350, 500 | 0, 400, 900, 1500 |

Figure 5

DESCRIPTION OF RADIOMIC FEATURES EXTRACTED

| Feature Category | Feature Type | Number of features extracted (total) | Relevance to PCa |
|---|---|---|---|
| Signal Intensity | T2w images, ADC maps | 1 x 2 (2) | Cancers are usually hypo-intense on mpMRI |
| First Order Statistics | Mean, Median, Sobel | 9 x 2 (18) | Intensity variability |
| Gabor | Frequency, Orientation | 80 x 2 (160) | Low-level oriented edges |
| Gray-level co-occurrence | Haralick | 3 x 13 x 2 (78) | Structural heterogeneity |
| Texture Energy | Laws' texture energy | 25 x 2 (50) | Appearance of ROI |

Figure 7

TOP 10 Peritumoral Radiomic Features (peritumoral alone) From bpMRI, In Low-vs-High, And Low-vs-All Settings (dataset 1, n = 210)

| Low-vs-All | | | Low-vs-High | | |
|---|---|---|---|---|---|
| Feature Name (Parameters) | Protocol | Radius (mm) | Feature Name (Parameters) | Protocol | Radius (mm) |
| Haralick (Entropy difference) | T2 | 6-9 | Haralick (Info measure 1) | T2 | 3-6 |
| Haralick (Momentum difference) | ADC | 6-9 | Haralick (Sum of Entropy) | ADC | 3-6 |
| Gabor (lambda = 3, theta = 0 rad) | T2W | 9-12 | Haralick (Correlation) | ADC | 3-6 |
| Haralick (Sum of Entropy) | T2W | 3-6 | Laws 9 | ADC | 9-12 |
| Haralick (Entropy difference) | ADC | 3-6 | Laws (12) | T2W | 3-6 |
| Haralick (Correlation) | ADC | 3-6 | Haralick (Info measure 2) | T2W | 3-6 |
| Haralick (Entropy difference) | ADC | 6-9 | Haralick (Entropy) | ADC | 3-6 |
| Gabor (wavelength = 3, orientation = 0.6 rad) | ADC | 9-12 | Laws (11) | ADC | 9-12 |
| Haralick (Info measure 2) | ADC | 3-6 | Laws (4) | ADC | 9-12 |
| Haralick (Info measure 1) | T2W | 6-9 | Haralick (Energy) | ADC | 3-6 |

Table 4: Top 10 Radiomic features (intratumoral and peritumoral) from biparametric MRI, in Low-vs-High, And Low-vs-All Settings

TOP 10 Radiomic Features (intratumoral and peritumoral) From bpMRI, in Low-vs-High, And Low-vs-All Settings

| Low-vs-High | | | | Low-vs-All | | |
|---|---|---|---|---|---|---|
| Feature Name (Parameters) | Protocol | Type | | Feature Name (Parameters) | Protocol | Type |
| Laws (15) | T2W | IT | | Gabor(6 Hz, 2.0 rad) | T2W | IT |
| Canny | T2W | IT | | Gabor(6 Hz, 2.8 rad) | T2W | PT |
| Collage (Entropy) | ADC | PT | | Haralick (Momentum Sum) | ADC | PT |
| Laws (11) | ADC | IT | | Gabor(6 Hz, 1.8 rad) | ADC | IT |
| Haralick (Entropy) | ADC | IT | | Mean | T2W | PT |
| Collage | ADC | IT | | Gabor(2.5 Hz, 0.4 rad) | T2W | IT |
| Haralick (Info measure 1) | T2W | PT | | Gabor(3 Hz, 0.4 rad) | T2W | IT |
| Laws (17) | ADC | PT | | Gabor(3.5 Hz, 0.4 rad) | T2W | IT |
| Haralick (Info measure 2) | T2W | IT | | Gabor(5 Hz, 1.6 rad) | ADC | IT |
| Haralick (Info measure 2) | ADC | IT | | Gabor(6 Hz, 1.6 rad) | ADC | IT |

Figure 13

Risk Stratification Results Of PCa Lesions For PIRADS v2 And Radiomics Based On D'Amico Criteria

| D'Amico Classification | PIRADS v2 | | Total | Combined Radiomic features (IT + PT) | |
|---|---|---|---|---|---|
| | High | Low | | High | Low |
| High-Risk | 48 | 6 | 54 | 39 | 15 |
| Intermediate-Risk | 51 | 20 | 71 | 46 | 25 |
| Low-Risk | 44 | 41 | 85 | 6 | 79 |
| Total | 143 | 67 | 210 | 91 | 119 |

Radiomic Features In Various Peritumoral Regions Of The Prostate Along With Corresponding Percentage of Epithelium, Lumen, And Stroma On Histopathology For Low, Intermediate, And High-Risk Patients Defined By D'Amico Criteria

| | Low-risk | | | Intermediate-risk | | | High-risk | | |
|---|---|---|---|---|---|---|---|---|---|
| peri-tumoral ring (mm) | 0-3 | 6-9 | 9-12 | 0-3 | 6-9 | 9-12 | 0-3 | 6-9 | 9-12 |
| Haralick IDM_T2W | | 0.11 | | | 0.12 | | | 0.25 | |
| Haralick Sum Avg_T2W | | 0.15 | | | 0.19 | | | 0.31 | |
| Haralick Sum Avg_ADC | 0.4 | | | 0.57 | | | 0.72 | | |
| Laws Edge Texture _ADC | | | -0.05 | | | -0.09 | | | -0.19 |
| % epithelium | 0.34 | 0.16 | 0.17 | 0.3 | 0.12 | 0.24 | 0.42 | 0.31 | 0.32 |
| % lumen | 0.27 | 0.15 | 0.1 | 0.22 | 0.13 | 0.16 | 0.24 | 0.21 | 0.14 |
| % stroma | 0.39 | 0.68 | 0.7 | 0.48 | 0.75 | 0.6 | 0.33 | 0.48 | 0.54 |

PREDICTING PROSTATE CANCER RISK OF PROGRESSION WITH MULTIPARAMETRIC MAGNETIC RESONANCE IMAGING USING MACHINE LEARNING AND PERITUMORAL RADIOMICS

CROSS REFERENCE TO RELATED APPLICATIONS

This application claims the benefit of U.S. Provisional Patent Application No. 62/691,090 filed Jun. 28, 2018, the contents of which are herein incorporated by reference in their entirety.

FEDERAL FUNDING NOTICE

This invention was made with government support under the grant(s) 1U24CA199374-01, R01 CA202752-01A1 R01 CA208236-01A1 R21 CA179327-01, R21 CA195152-01, R01 DK098503-02, R01 CA216579-01A1, R01 CA220581-01A1, 1 C06 RR12463-01, and VA IBX004121A awarded by the National Institutes of Health. Also awards W81XWH-15-1-0558, W81XWH-16-1-0329, and W81XWH-17-PCRP-IDA awarded by the Department of Defense. The government has certain rights in the invention.

BACKGROUND

Prostate cancer (PCa) is the second most common cancer in men in the United States, with new diagnoses and death estimates of 164,690 and 29,430 in 2018, respectively. The course of treatment for PCa patients may be based on their risk of PCa progression as determined using clinical parameters. Clinical parameters may include serum prostate specific antigen (PSA), biopsy Gleason Score (GS), and digital rectal examination. The D'Amico Risk Classification System (DRCS) is widely used for assessing risk of PCa progression based on clinical parameters. The DRCS may be further considered in identifying patients who might benefit from radical therapy versus active surveillance.

Multi-parametric magnetic resonance imaging (mpMRI) is increasingly used in PCa detection and characterization. Prostate Imaging and Reporting Data Standard (PIRADS) guidelines have been established to streamline the process of identifying clinically significant PCa in MRI imagery. However, PIRADS evaluations may suffer from poor inter-rater reliability, and statistically vary depending on a radiologist's experience or ability to interpret prostate MRI. For example, PCa detection rate may fall below 15% for PIRADS 3 cases. Furthermore, PIRADS becomes of limited value when assessing lesions having a volume less than 0.5 cm$^3$.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIG. 5 illustrates a table describing a dataset and the number of lesions corresponding to each site employed by various embodiments discussed herein.

FIG. 7 illustrates a table describing radiomic features and their significance in characterizing PCa according to various embodiments discussed herein.

FIG. 11 illustrates a table of peritumoral radiomic features selected from bi-parametric MRI (bpMRI) imagery, in Low-versus-High, and Low-versus-All settings according to various embodiments discussed herein.

FIG. 13 illustrates a table describing ten radiomic features (intratumoral and peritumoral) extracted from bpMRI imagery, in Low-versus-High, and Low-versus-All settings according to various embodiments discussed herein.

FIG. 14 illustrates a table describing risk stratification results of PCa lesions for PIRADS v2 and radiomics based on D'Amico criteria according to various embodiments discussed herein.

FIG. 15 illustrates a table 1500 describing radiomic features in various peritumoral regions of the prostate along with corresponding percentages of epithelium, lumen, and stroma on histopathology for low, intermediate, and high risk PCa patients defined by D'Amico criteria according to various embodiments discussed herein.

DETAILED DESCRIPTION

Figure 1:
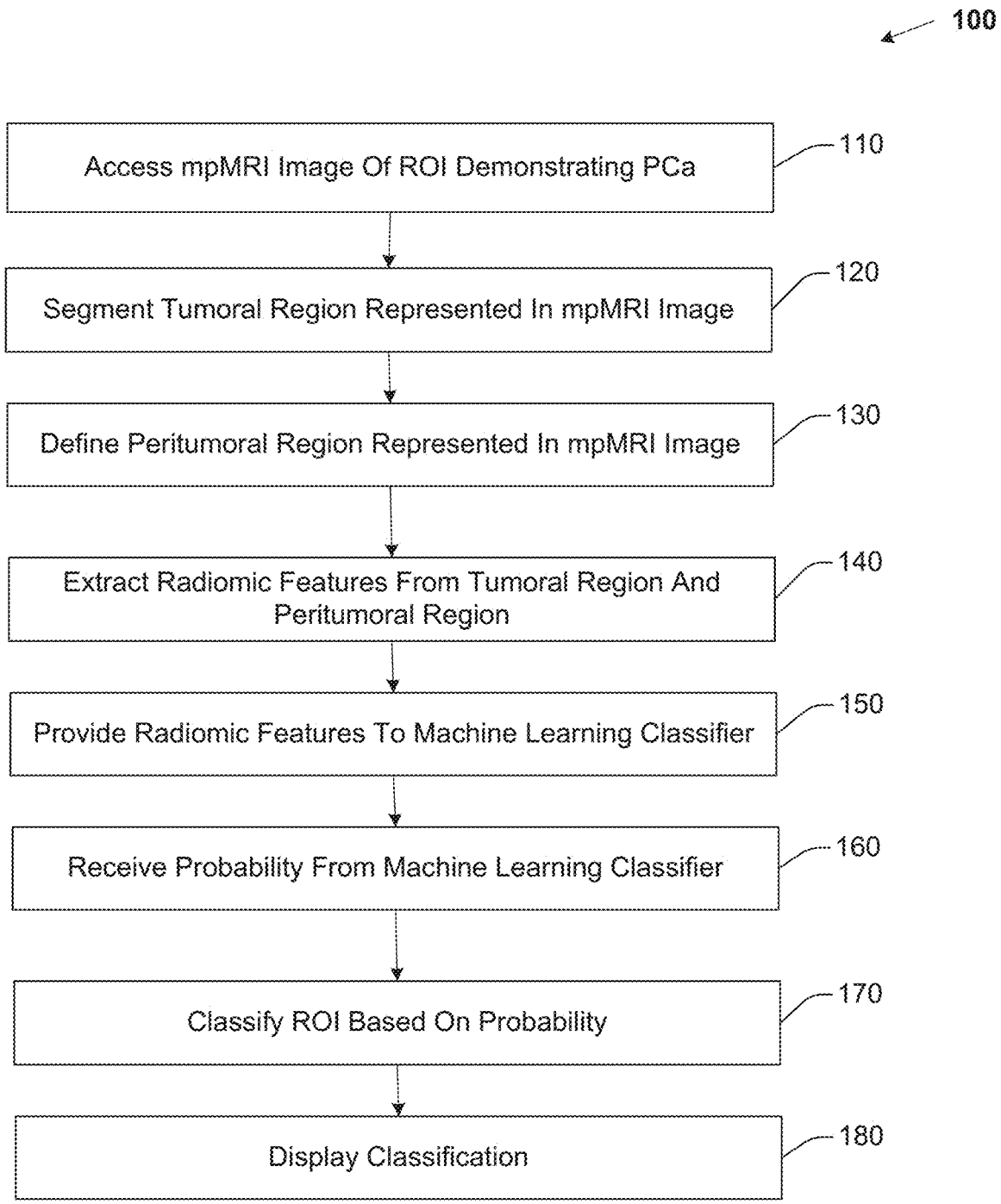
FIG. 1 illustrates a flow diagram of an example method or set of operations that employs a machine learning classifier to classify a region of interest (ROI) demonstrating prostate cancer (PCa) according to various embodiments discussed herein.

Radiomic features extracted from medical imagery, including magnetic resonance imaging (MRI) imagery may be employed for prostate cancer (PCa) characterization or risk-stratification in vivo. Radiomics includes the computerized extraction of and analysis of sub-visual attributes from radiographic imagery (e.g., MRI, multi-parametric MRI (mpMRI), bi-parametric MRI (bpMRI), computed tomography (CT)), and the quantification of phenotypic characteristics of a region of interest (ROI) (e.g., lesion, tumor) represented in the imagery based on the extracted features. However, existing approaches in employing radiomic features derived from staging mpMRI for PCa risk stratification typically examine textural patterns only from within a tumoral region (i.e., an intratumoral (IT) region) or within a tumor ROI. Existing approaches thus may ignore other areas represented in the radiographic imagery, including the peritumoral region that immediately surrounds the intratumoral region, that may contain useful information. Existing approaches to predicting PCa risk that do not consider the peritumoral region may therefore be less than optimal.

Embodiments described herein can employ techniques discussed herein for prediction of PCa risk via a machine learning classifier trained on radiological imagery (e.g., MRI, mpMRI, bpMRI) and radiomic features extracted from said imagery that have been identified as distinguishing between low-risk, intermediate risk, or high risk lesions (e.g., tumors). In various embodiments, radiomic features employed by various embodiments may include intratumoral and peritumoral radiomic features. Embodiments may employ peritumoral radiomic features that quantify heterogeneity patterns from the peritumoral region as an independent predictor of PCa progression risk. Embodiments may further employ tumoral radiomic features and peritumoral radiomic features to predict PCa progression risk categories as defined by D'Amico Risk Classification System (DRCS) criteria.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Various embodiments can employ techniques discussed herein to facilitate determination of a risk of PCa progression. FIG. 1 illustrates is a flow diagram of a first example method or set of operations 100 that employs a machine learning classifier to generate a prediction of PCa progression risk based on intratumoral and peritumoral radiomic features extracted from a radiological image, according to various embodiments discussed herein. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations or methods described herein. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 100 includes, at 110, accessing a multi-parametric magnetic resonance imaging (mpMRI) image associated with a patient. The mpMRI image includes a region of interest (ROI) demonstrating prostate cancer (PCa) pathology. The mpMRI image has a plurality of pixels, a pixel having an intensity. The mpMRI image includes a representation of a tumoral region. The accessed mpMRI image can be stored in memory locally or remotely, and can be obtained via a medical imaging device one of concurrently with method 100 (e.g., via a medical imaging device implementing method 100) or prior to method 100. Accessing the mpMRI image includes acquiring electronic data, reading from a computer file, receiving a computer file, reading from a computer memory, or other computerized activity not practically performed in the human mind. In one embodiment, the mpMRI image is a bi-parametric MRI (bpMRI) image comprising a T2W MRI image and an apparent diffusion coefficient (ADC) map. The bpMRI image may include a plurality of voxels, a voxel having an intensity.

The set of operations 100 also includes, at 120, segmenting a tumoral region represented in the image. Segmenting the tumoral region includes defining a tumoral boundary. In one embodiment, the tumoral region is segmented using a watershed segmentation technique, a region growing or active contour technique, or a convolutional neural network (CNN) approach. In another embodiment, the tumoral region may be segmented by a radiologist. In another embodiment, the image includes a defined tumor volume having a boundary and a centroid, and thus step 120 may, in one embodiment, be skipped. For example, the tumoral region may be segmented via a medical imaging device one of concurrently with method 100 (e.g., via a medical imaging device implementing method 100) or prior to method 100. Segmenting the tumoral region includes acquiring electronic data, reading from a computer file, receiving a computer file, reading from a computer memory, or other computerized activity not practically performed in the human mind.

The set of operations 100 also includes, at 130, defining a peritumoral region based on the tumoral boundary. In one embodiment, defining the peritumoral region includes performing a dilation of the tumoral boundary. The peritumoral region includes a plurality of annular rings. In one embodiment, performing a dilation of the tumoral boundary includes dilating the tumoral boundary 12 mm. In this embodiment, the peritumoral region includes four annular rings. The annular rings may each be 3 mm annular rings. For example, in this embodiment, the peritumoral region includes a first annular ring from 0 mm to 3 mm from the tumoral boundary, a second annular ring from 3 mm to 6 mm, a third annular ring from 6 mm to 9 mm, and a fourth annular ring from 9 mm to 12 mm. In another embodiment, performing a dilation of the tumoral boundary includes dilating the tumoral boundary another, different amount (e.g., 9 mm, 15 mm), and the peritumoral region may include other, different numbers of annular rings, or annular rings having different sizes (e.g., 2 mm, 5 mm). Defining the peritumoral region includes acquiring electronic data, reading from a computer file, receiving a computer file, reading from a computer memory, or other computerized activity not practically performed in the human mind.

Figure 4A:
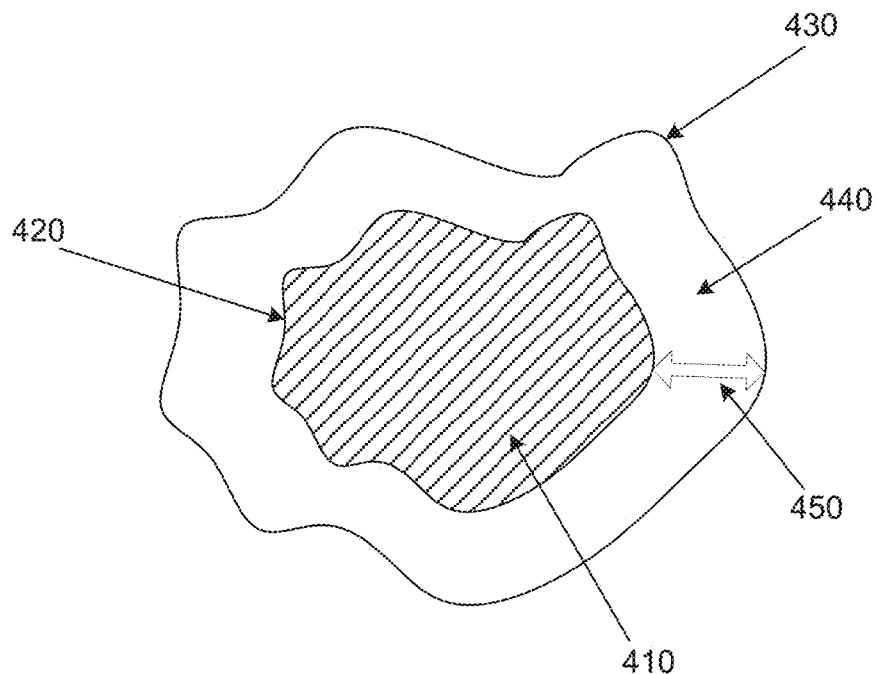
FIG. 4A and FIG. 4B illustrate a tumoral region and an associated peritumoral region.

FIG. 4A illustrates an example tumoral region 410. A tumor represented in a radiological image as described herein has a tumoral boundary. Embodiments define a peritumoral region based on a morphological transformation of the tumoral boundary. A peritumoral region may be defined as the region surrounding the tumoral region out to a distance. For example, in one embodiment, the peritumoral region may be the region extending 2 mm from the tumoral boundary. In another embodiment, the peritumoral region may be the region extending 6 mm from the tumoral boundary, or 12 mm from the tumoral boundary. The peritumoral region may be defined by a distance measured in mm, as described, or in other units, including pixels.

FIG. 4A illustrates an example peritumoral region 440 associated with a PCa lesion or tumoral region 410. Peritumoral region 440 is bounded by outer peritumoral boundary 430 and tumoral boundary 420. In one embodiment, example operations, methods, and apparatus morphologically dilate tumoral boundary 420 by an amount 450, resulting in the outer peritumoral boundary 430. Amount 450 may be, for example, 2 mm, 4 mm, 6 mm, 6 pixels, 12 pixels, or another, different amount.

In another embodiment, the peritumoral boundary may be generated using other techniques. For example, the peritumoral boundary may be defined as a function of a property of the tumor. The property of the tumor may include, for example, a diameter, a radius, a perimeter, an area, a volume, or other property of the tumor. The function may define the peritumoral region as, for example, a morphologic dilation of the tumoral boundary, where the dilation ratio is defined by a magnitude of an axis of the tumor. In another embodiment, the peritumoral boundary may be defined as a disc of a threshold radius defined about the centroid of the tumor, or defined on the focal points of an elliptical representation of the tumor. In one embodiment, the peritumoral boundary may be manually defined. Other approaches or combinations of approaches may be used to define the peritumoral boundary.

Figure 4B:
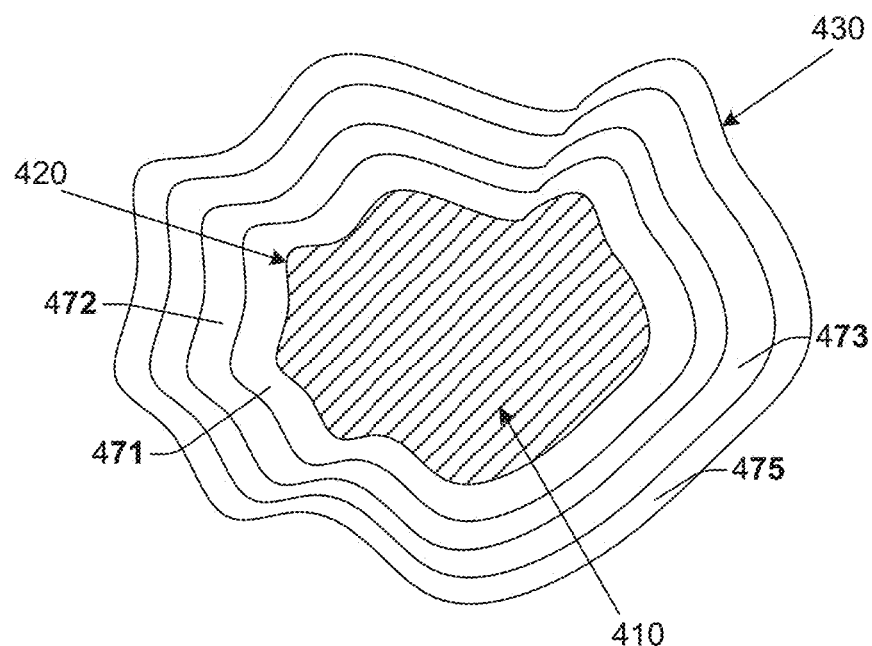

In one embodiment, the peritumoral region is defined using 3 mm annular rings defined about the boundary of the tumoral region out to a radius of 12 mm from the boundary. FIG. 4B illustrates an example peritumoral region that includes four annular rings 471, 472, 473, and 475 defined from the peritumoral boundary 420. Annular ring 471 extends from 0 mm to 3 mm from the tumoral boundary. Annular ring 472 extends from 3 mm to 6 mm from the tumoral boundary. Annular ring 473 extends from 6 mm to 9 mm from the tumoral boundary. Annular ring 475 extends from 9 mm to 12 mm from the tumoral boundary. In another embodiment, other annular ring sizes, radii, numbers of bands or rings, or techniques may be employed to define the peritumoral region.

Returning to FIG. 1, the set of operations 100 also includes, at 140, extracting a set of radiomic features from the image. The set of radiomic features includes at least one radiomic feature extracted from the peritumoral region, and at least one, different radiomic feature extracted from the tumoral region. Extracting the set of radiomic features includes acquiring electronic data, reading from a computer file, receiving a computer file, reading from a computer memory, or other computerized activity not practically performed in the human mind. In various embodiments, the set of radiographic features may include N (N being a positive integer, e.g., 10, or a greater or lesser number) radiomic features that have been identified (e.g., via an feature selection approach or measure such as minimum redundancy maximum relevance (mRMR), Wilcoxon rank sum, etc.) as the N most distinguishing or discriminating radiomic features for distinguish a first class (e.g., low-risk of PCa progression) from a second, different class (e.g., high-risk of PCa progression, high-risk and intermediate-risk of PCa progression).

The set of operations 100 also includes, at 150, providing the set of radiomic features to a machine learning classifier trained to distinguish a first class from a second, different class, based on the set of radiomic features. In one embodiment, the machine learning classifier is a quadratic discriminant analysis (QDA) classifier. In another embodiment, the machine learning classifier is a support vector machine (SVM) classifier. In another embodiment, other types of machine learning classifier may be employed, including, for example, a linear discriminant analysis (LDA) classifier, a random forests (RF) classifier, or a deep learning classifier, including a convolutional neural network (CNN). In one embodiment, the set of operations 100 further includes computing first order statistics associated with each of the members of the set of radiomic features, respectively. Providing the set of radiomic features may, in this embodiment, include providing the first order statistics to the machine learning classifier. Providing the set of radiomic features to the machine learning classifier includes acquiring electronic data, reading from a computer file, receiving a computer file, reading from a computer memory, or other computerized activity not practically performed in the human mind.

The set of operations 100 also includes, at 160, receiving, from the machine learning classifier, a probability that the ROI is a member of the first class. The machine learning classifier computes the probability (e.g., posterior class probability) based on the set of radiomic features. In one embodiment, the machine learning classifier computes the probability based on the set of radiomic features and the first order statistics. Receiving the probability from the machine learning classifier includes acquiring electronic data, reading from a computer file, receiving a computer file, reading from a computer memory, or other computerized activity not practically performed in the human mind.

The set of operations 100 also includes, at 170, classifying the ROI as a member of the first class or the second, different class based, at least in part, on the probability. In various embodiments, the classification may include one or more of a most likely outcome (e.g., as determined based on the radiomic features, etc.) such as low-risk of progression or high-risk of progression; a probability or confidence associated with a most likely outcome; and/or associated probabilities/confidences associated with each of a plurality of outcomes (e.g., low-risk of PCa progression, intermediate-risk of PCa progression, high-risk of PCa progression). In various embodiments, classifying the ROI may include classifying the patient associated with the image as a member of the first class or the second, different class.

In one embodiment, the first class is low-risk of progression, and the second class is high-risk of progression. In this embodiment, the set of radiomic features includes: an intratumoral Laws (15) feature extracted from the T2W image, an intratumoral Canny feature extracted from the T2W image, a peritumoral co-occurrence of local anisotropic gradient orientations (CoLIAGe) entropy feature extracted from the ADC map, an intratumoral Laws (11) feature extracted from the ADC image, an intratumoral Haralick (entropy) feature extracted from the ADC map, an intratumoral CoLIAGe feature extracted from the ADC map, a peritumoral Haralick (info measure 1) feature extracted from the T2W image, a peritumoral Laws (17) feature extracted from the ADC map, an intratumoral Haralick (info measure 2) feature extracted from the T2W image, and an intratumoral Haralick (info measure 2) feature extracted from the ADC map.

In another embodiment, the first class is low-risk of progression, and the second class is intermediate risk of progression or high risk of progression. In this embodiment, the set of radiomic features includes an intratumoral Gabor (6 Hz, 2.0 rad) feature extracted from the T2W image, a peritumoral Gabor (6 Hz, 2.8 rad) feature extracted from the T2W image, a peritumoral Haralick (momentum sum) feature extracted from the ADC map, an intratumoral Gabor (6 Hz, 1.8 rad) feature extracted from the ADC map, a mean filter (3 pixel by 3 pixel window) response feature extracted from the peritumoral region of the T2W image, an intratumoral Gabor (2.5 Hz, 0.4 rad) feature extracted from the T2W image, an intratumoral Gabor (3 Hz, 0.4 rad) feature extracted from the T2W image, an intratumoral Gabor (3.5 Hz, 0.4 rad) feature extracted from the T2W image, an intratumoral Gabor (5 Hz, 1.6 rad) feature extracted from the ADC map, and an intratumoral Gabor (6 Hz, 1.6 rad) feature extracted from the ADC map. A mean filter (3 pixel by 3 pixel window) response feature extracted from the peritumoral region of the T2W image is a smoothing filter which provides a low resolution representation of the T2W image. In another embodiment, the set of radiomic features may include other, different radiomic features.

The set of operations 100 further includes, at 180, displaying the classification. Displaying the classification and optionally displaying one or more of the set of radiomic features, the probability, or the image may include displaying the classification and optionally displaying one or more of the set of radiomic features, the probability, or the image on a computer monitor, a smartphone display, a tablet display, or other displays. Displaying the classification and optionally displaying one or more of the set of radiomic features, the probability, or the image can also include printing the classification and optionally displaying one or more of the set of radiomic features, the probability, or the image. Displaying the classification and optionally displaying one or more of the set of radiomic features, the probability, or the image can also include controlling a PCa risk prediction system, a personalized medicine system, a monitor, or other display, to display operating parameters or characteristics of a machine learning classifier, during at least one of training and testing of the machine learning classifier, or during clinical operation of the machine learning classifier. By displaying the classification and optionally displaying one or more of the set of radiomic features, the probability, or the image, example embodiments provide a timely and intuitive way for a human medical practitioner to more accurately classify PCa or stratify PCa progression risk, thus improving on existing approaches to predicting PCa risk of progression. Embodiments may further display operating parameters of the machine learning classifier.

Figure 2:
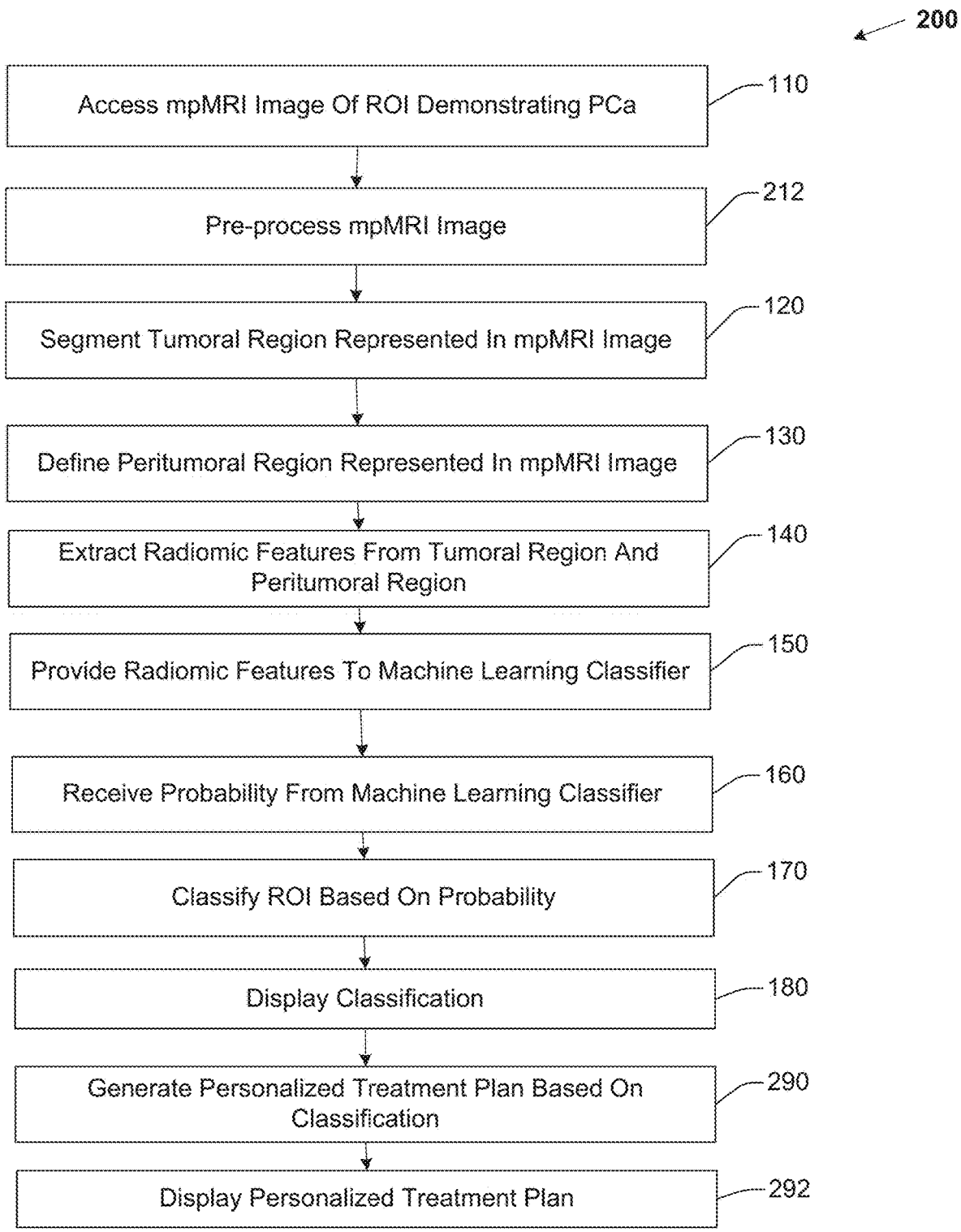
FIG. 2 illustrates a flow diagram of an example method or set of operations that employs a machine learning classifier to classify an ROI demonstrating PCa according to various embodiments discussed herein.

FIG. 2 illustrates a set of operations 200 that is similar to operations 100 but that includes additional operations. Operations 200 includes, at 212, preprocessing the image.

Figure 3:
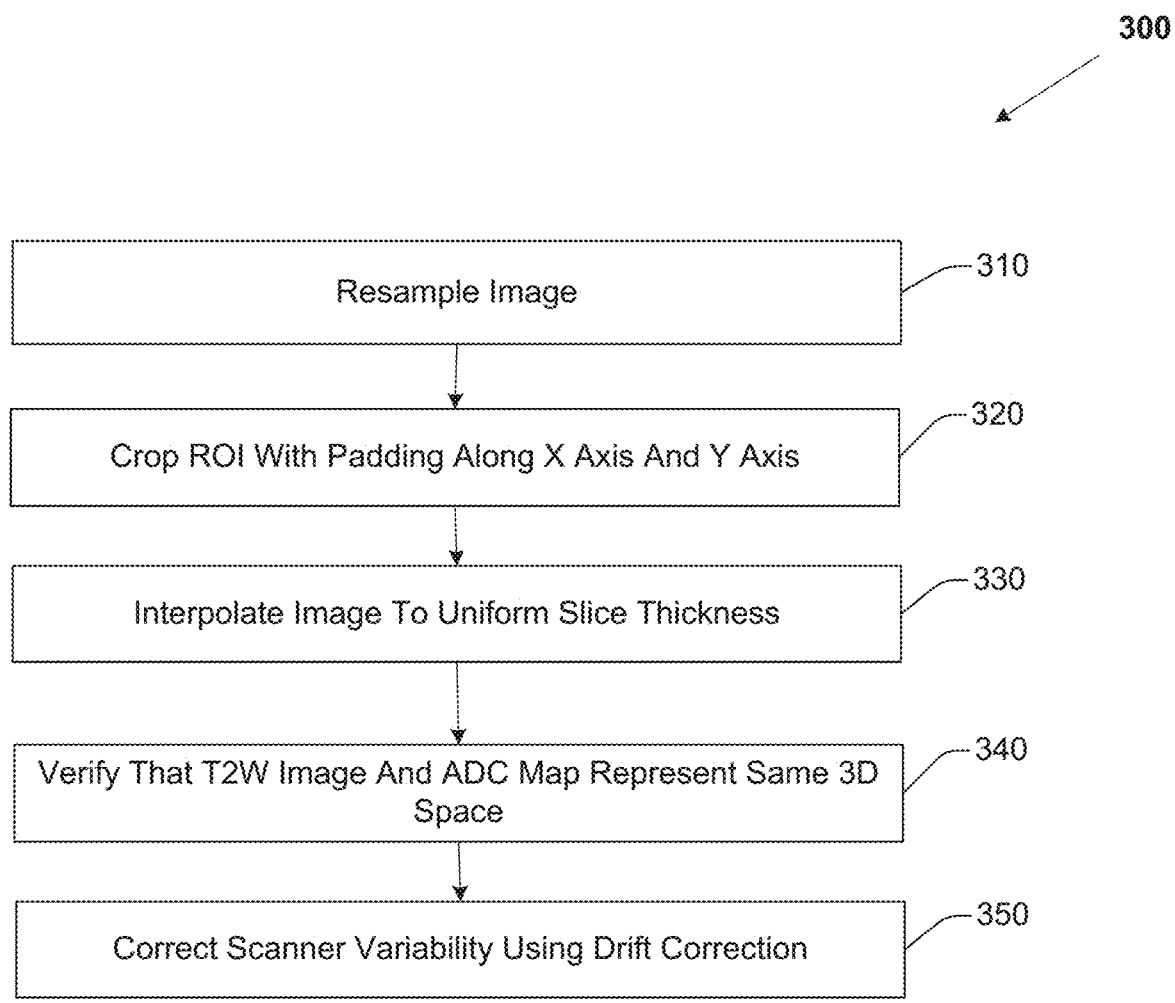
FIG. 3 illustrates a flow diagram of an example method or set of operations for preprocessing a multi-parametric magnetic resonance imaging (mpMRI) image, according to various embodiments discussed herein.

FIG. 3 illustrates a method or set of operations 300 for preprocessing an image, including an mpMRI image or bpMRI image as employed by embodiments described herein. Operations 300 includes, at 310, resampling the image. In one embodiment, resampling the image includes resampling the image to a pixel size of 0.5×0.5 mm². Operations 300 also includes, at 320, cropping the ROI. In one embodiment, cropping the ROI includes cropping the ROI with 2 mm padding along the x axis and y axis. Operations 300 also includes, at 330, interpolating the image to a consistent slice thickness. In one embodiment, interpolating the image includes interpolating the image to a 3 mm slice thickness. Operations 300 also includes, at 340, verifying that the T2W image and ADC map represent the same three dimensional (3D) space. Operations 300 further includes, at 350, correcting scanner variability using a drift correction approach.

Returning to FIG. 2, the set of operations 200 may further include, at 290, generating a personalized PCa treatment plan. The personalized PCa treatment plan can be generated based, at least in part, on the classification and optionally on one or more of the set of radiomic features, the probability, or the image. The personalized PCa treatment plan may be generated for the patient of whom the image was acquired (e.g., the patient associated with the image) based, at least in part, on the classification and optionally on one or more of the set of radiomic features, the probability, or the image. Defining a personalized PCa treatment plan facilitates delivering a particular treatment that will be therapeutically active to the patient, while minimizing negative or adverse effects experienced by the patient. For example, the personalized PCa treatment plan may suggest a surgical treatment, may define a pharmaceutical agent dosage or schedule and/or other recommendations for PCa management, for a patient, wherein the specific recommendation can depend on whether or not the patient is likely to experience PCa progression. Generating the personalized PCa treatment plan includes acquiring electronic data, reading from a computer file, receiving a computer file, reading from a computer memory, or other computerized activity not practically performed in the human mind.

The set of operations 200 may further comprise, at 292, displaying the personalized PCa treatment plan according to embodiments described herein.

Figure 20:
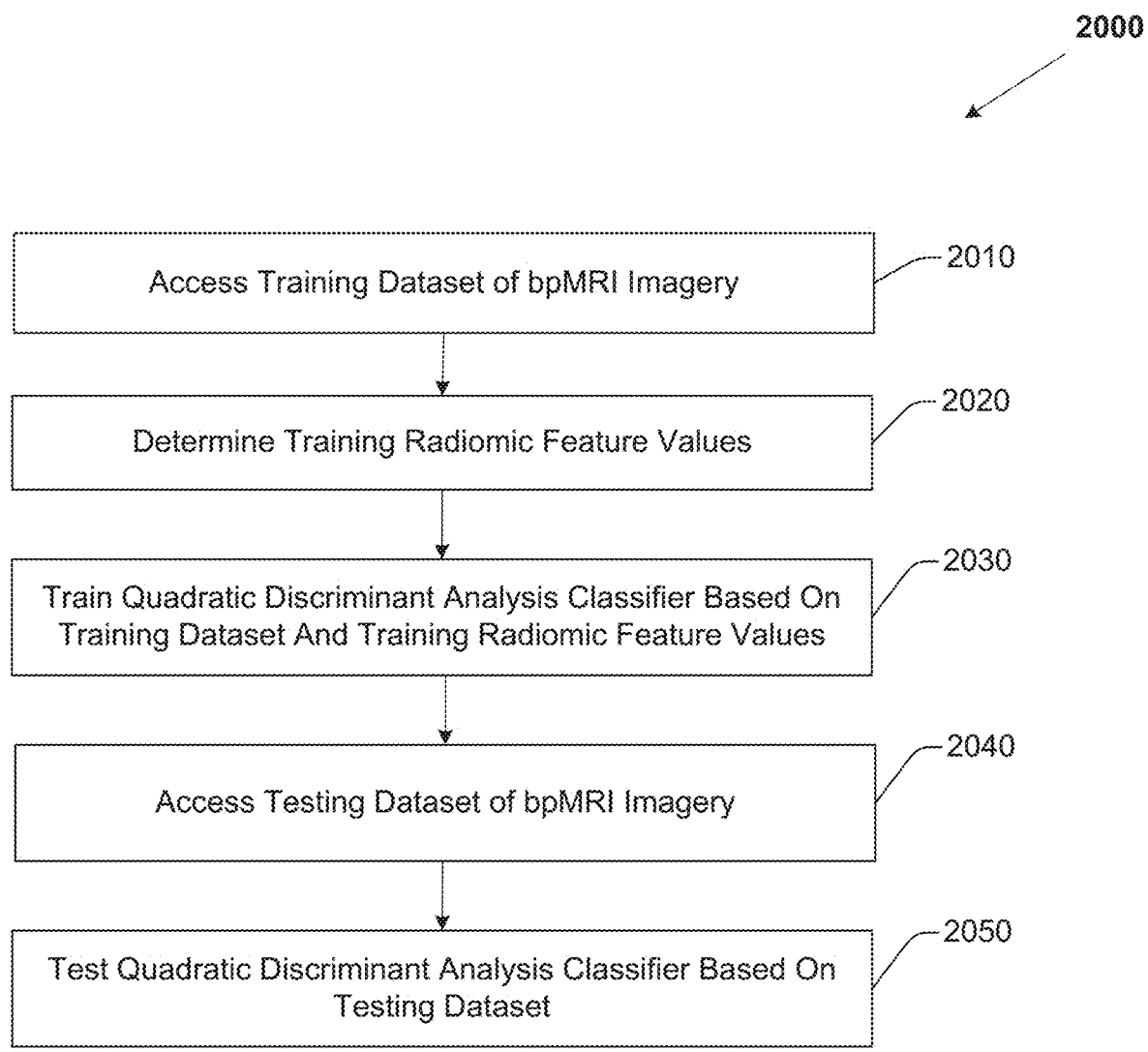
FIG. 20 illustrates a flow diagram of an example method or set of operations for training a machine learning classifier according to various embodiments discussed herein.

Referring to FIG. 20, illustrated is a diagram showing an example flow of a method or set of operations 2000 that facilitates training of a machine learning classifier to generate a probability that a patient associated with an ROI demonstrating PCa has a low-risk of progression, intermediate-risk of progression, or high-risk of progression, based on radiomic features extracted from radiographic (e.g., MRI, mpMRI, bpMRI) image(s), according to various embodiments discussed herein.

The set of operations 2000 may include, at 2010, accessing a training dataset of mpMRI or bpMRI images of tissue demonstrating PCa. In one embodiment, the training dataset includes a multi-institutional cohort. As explained in greater detail herein, the training dataset may include a plurality of mpMRI or bpMRI images comprising a positive set that is associated with a first classification (e.g., low-risk of PCa progression) and a negative set that is associated with a different second classification (e.g., high-risk of PCa progression, or high-risk or intermediate risk of PCa progression). Embodiments using a multi-institutional cohort have improved, more robust predictive accuracy with respect to variations in imaging parameters, including image resolution, compared to existing approaches. Embodiments using a multi-institutional cohort further have improved generalizability compared to existing approaches, since embodiments may not be restrictively optimized to data acquired from a specific institution.

The set of operations 2000 may further include, at 2020, determining, for each image in the training dataset, values for that image for each of the N (N being a positive integer) most distinguishing radiomic features for predicting PCa progression. The N most distinguishing radiomic features can be determined via any of a variety of algorithms or measures (e.g., RF, t-test, Wilcoxon, mRMR, etc.). In one embodiment, N has a value of ten. In one embodiment, first order statistical values may be computed for each of the N most distinguishing radiomic features.

The set of operations 2000 may further include, at 2030, training a machine learning classifier (e.g., QDA (Quadratic Discriminant Analysis classifier), SVM (Support Vector Machine), LDA (Linear Discriminant Analysis) classifier, DLDA (Diagonal Line Discriminant Analysis) classifier, RF (Random Forest) classifier, CNN (Convolutional Neural Network) classifier, etc.) based on the training dataset, and, for each image in the training dataset, the values of the N radiomic features for that image, and a known outcome (e.g., PCa progression or non-progression) associated with that image. Based on the training dataset, and, for each image in the training dataset, the values of the N radiomic features for that image, and a known outcome (e.g., PCa progression or non-progression) associated with that image, the classifier can determine classes for PCa progression or non-progression, and probability of PCa progression or non-progression for associated feature vectors (e.g., comprising N values of radiomic features). In one embodiment, the classifier is additionally trained with the first order statistical values computed for each of the N most distinguishing radiomic features.

The set of operations 2000 may optionally include, at 2040, accessing a testing dataset. The testing dataset includes mpMRI images of tissue demonstrating PCa for which outcomes for a patient associated with each image are known (e.g., in a manner similar to set of operations 100 or 200, additionally including comparing a generated classification with the known outcome).

The set of operations 2000 may optionally include, at 2050, testing the machine learning classifier on the testing dataset. In this manner, the ability of the machine learning classifier to correctly classify MRI imagery, including mpMRI or bpMRI images of tissue demonstrating PCa can be estimated. In one embodiment, the test dataset includes a multi-institutional cohort.

Training the machine learning classifier can also include determining which radiomic features are most discriminative in distinguishing risk of progression in PCa. Training the machine learning classifier may also include determining the optimal combination of parameters used in the computation of the probability that can best separate a positive class from a negative class (e.g., a low-risk of PCa progression or high-risk of PCa progression).

Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed. Training the machine learning classifier may also include determining the optimal combination of parameters used in the computation of a probability of PCa progression risk (e.g., maximum peritumoral radius to include, size and number of annular subregions analyzed, or number of radiomic features to extract) to best separate a positive and negative class.

Techniques and aspects of various embodiments are further explained below, in connection with an example embodiment that facilitates determination of a risk of PCa progression for a patient represented in mpMRI imagery.

Figure 6:
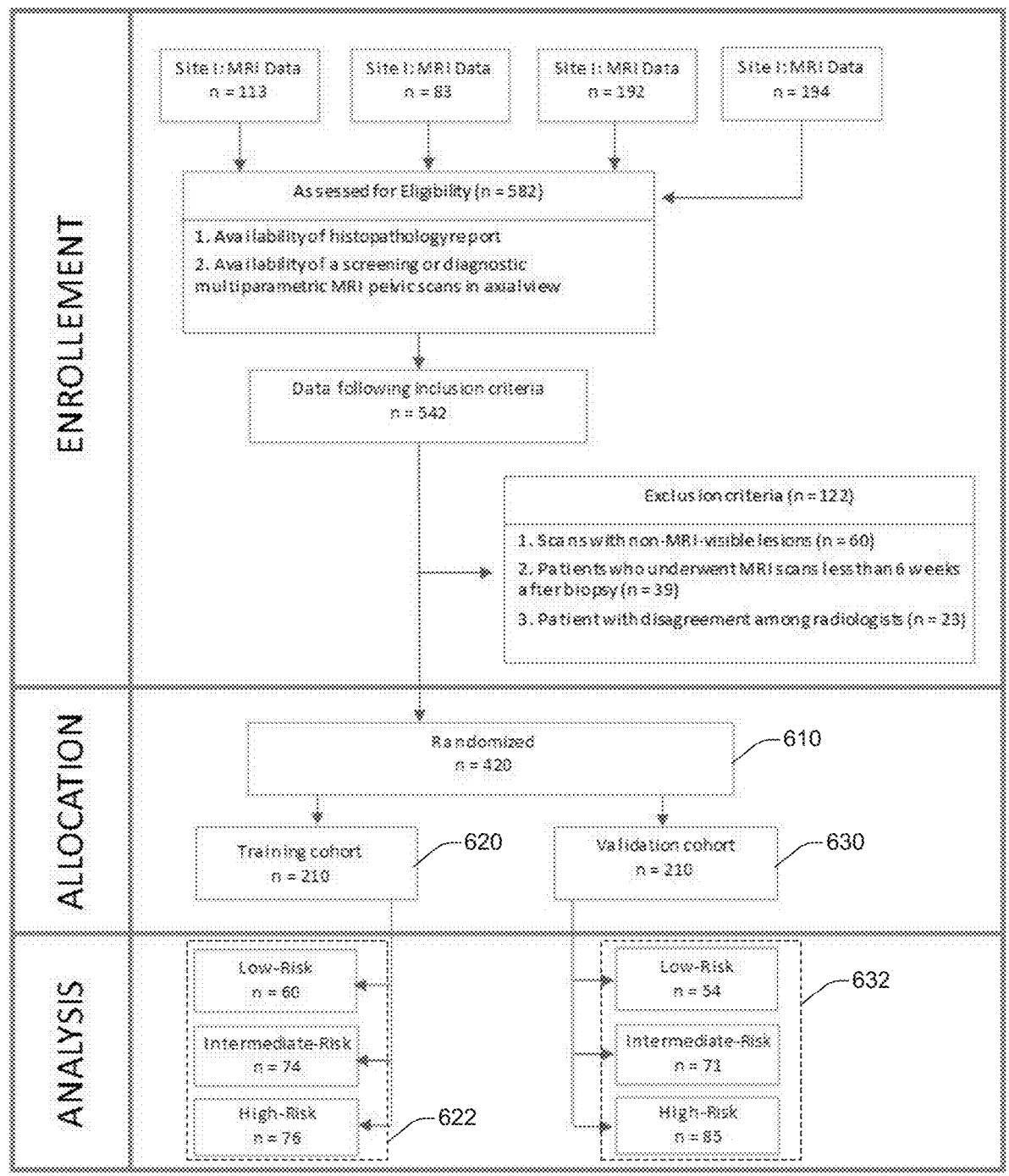
FIG. 6 illustrates a flow diagram of an example method or set of operations for selecting a cohort employed by various embodiments discussed herein.

Example Use Case: A Combination of Intratumoral and Peritumoral Radiomic Features Extracted From MRI Predict Prostate Cancer Risk An example embodiment included training a machine learning classifier to predict risk of prostate cancer (PCa) based on example cases of low-risk of progression, intermediate risk of progression, and high-risk of progression lesions (e.g., tumors). In this example, biopsy-confirmed PCa lesions of patients from four different institutions (institution 1, institution 2, institution 3, institution 4) were retrospectively analyzed. FIG. 6 illustrates a flow diagram of an example method or set of operations for selecting a cohort employed by various embodiments discussed herein. Patients from all four institutions underwent 3T mpMRI scans and systematic 12-core TRUS-guided biopsies. Inclusion criteria included (a) availability of histopathology report, (b) ability to estimate the D'Amico risk for each patient's most dominant lesion, and (c) presence of a screening or diagnostic MRI scans (e.g., T2W images and ADC maps) in the axial view. A total of 582 lesions from 406 patients were thus identified. FIG. 5 illustrates a table 500 that illustrates the dataset and the number of lesions corresponding to each site (e.g., institution).

To this cohort of 582 lesions, the following exclusion criteria were applied: (1) removing scans with non-MRI-visible lesions, (2) excluding patients who underwent MRI scans less than six weeks after biopsy in order to avoid hemorrhage artifacts in images, and then (3) analyzing only lesions which were assigned to the same PIRADS category by at least two radiologists, to minimize the adverse effect of inter-observer variability of PIRADS assessment. General agreement (each scoring PIRADS 1-2, 3, and 4-5) between at least 2 out of the 3 radiologists was 85%. The final cohort 610 comprised of N=420 lesions from 291 patients. The final cohort 610 was divided into a first group 620 for training a machine learning classifier, and second group 630 for testing the machine learning classifier. Lesions from the first group 620 were used to train machine learning classifiers. Lesions from the second group 630 were used for independent validation of the machine learning classifiers. These remaining lesions were segregated into three groups of low-risk, intermediate-risk, and high-risk of PCa progression according to DRCS, illustrated at 622 for the training group and 632 for the testing group, respectively.

Additionally, for studying the association between peritumoral radiomic features and histopathological attributes, three more patients, one each belonging to low-risk, intermediate-risk, and high-risk of PCa progression DRCS categories were identified from a separate cohort of 18 patient studies (from Institution 3) who underwent 3T mpMRI scan prior to radical prostatectomy (RP).

In this example, all the prostate MRI scans were independently reviewed by three expert radiologists: R1, R2, and R3 (having 7, 10, and 15 years of experience, respectively) and delineated lesion regions of interest (ROI) regions which were confirmed to have PCa from biopsy. To minimize bias, radiologists were given only positive core locations from the biopsy reports without any information about the biopsy findings.

In this example, lesions were also assessed according to the PIRADS v2 reporting criteria. ROIs were assigned a score of 1 to 5 for each MRI parameter (T2W, DCE, and DWI) and then an overall impression ROI score (based on individual parameter scores) was deduced. Lesions were divided into three groups: (a) low-(PIRADS 1, 2), (b) intermediate-(PIRADS 3), and (c) high-clinical significance (PIRADS 4, 5) (LCS, ICS, and HCS, respectively).

In this example, images are pre-processed. In other examples, images may be optionally pre-processed. For each lesion in the cohort, each slice from T2W MRI and ADC maps was resampled to a uniform pixel size of $0.5 \times 0.5$ mm$^2$. Then, images were cropped to the lesion region of interest (in this example, with 4 pixels (2 mm) padding along the x and y directions) using the available prostate masks from segmentation. Similarly, all volumes were interpolated to 3 mm slice thickness to account for resolution differences during acquisition. Then, all the volumes of T2W and ADC sequences were visually verified to ensure they occupied the same 3D space. Images were corrected for inherent scanner variability using a drift correction algorithm. Inherent scanner variability refers to the inherent drift between different MRI acquisitions, which causes image intensity values to lack tissue-specific meaning between studies. Studies acquired using an endo-rectal coil were bias field corrected.

In this example, radiomic features are extracted from the mpMRI imagery. In this example, 75 two-dimensional (2D) radiomic texture features (including first-order statistics, statistical, gray-level co-occurrence, steerable Gabor, entropy, edge detection and, Laws energy) were extracted for PCa localization from bpMRI imagery that includes T2W images and ADC maps. A summary of these radiomic features and their significance in characterizing PCa is illustrated in table 700 in FIG. 7. All features were implemented in MATLAB (Mathworks, Inc. Natick, Mass.) and were calculated within the PCa ROIs for each of the T2W MRI and ADC maps.

Figure 8:
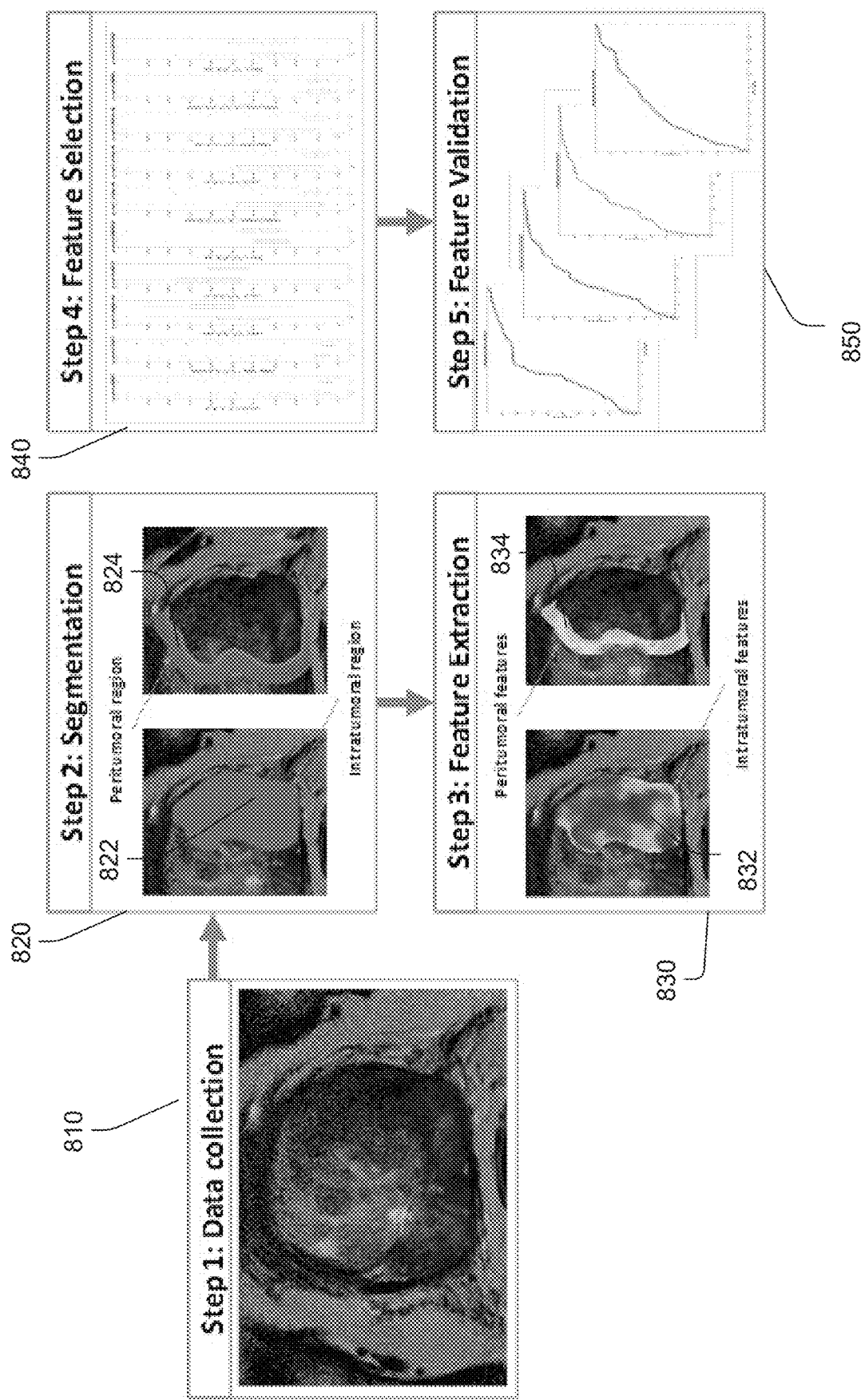
FIG. 8 illustrates a flow diagram of an example method or operations according to various embodiments discussed herein.

In this example, four first-order statistics (mean, standard deviation, skewness, and kurtosis) are calculated for radiomic features from each PCa ROI which are then normalized to values between 0 and 1. This leads to the extraction of six-hundred (600) radiomic features (three-hundred (300) for each of T2W and ADC) intratumorally. Similarly, 2400 features from four peritumoral rings of 3 mm radius increments were extracted, leading to having a total of 3000 texture features for each lesion (1500 per MRI protocol, e.g. T2W MRI and ADC map). This is illustrated in FIG. 8. At 810, MRI images are retrospectively collected as described herein. ROIs are segmented in axial view at 820 to obtain intratumoral masks 822 (e.g., tumoral boundary) as described herein. Peritumoral regions 824 (e.g., masks) are defined for varying distances outside the tumoral boundary, and radiomic features are extracted at 830 from the intratumoral regions 832 and peritumoral regions 834. Feature selection approaches, including, in this example, a Wilcoxon rank-sum test and mRMR feature selection are applied at 840 to select the top N (e.g., ten in this example) most discriminatory radiomic features (e.g., Haralick, Laws energy, Gabor texture features) which are used to train a machine learning classifier. Validation of results on an independent testing or validation dataset is illustrated at 850 by AUC graphs.

In this example, a two-sided Wilcoxon rank-sum test was applied to all extracted radiomic features where the null hypothesis is that features in low-risk and high-risk groups are samples from continuous distributions with equal medians, against the alternative that they are not. The Wilcoxon rank-sum test assumes that the two samples are independent which enables them to have different lengths. Those radiomic features with p-value<0.01 were used for selecting the best set of discriminating features using a minimum redundancy, maximum relevance algorithm (mRMR) feature selection approach. MRMR was used to identify and rank a set of the ten most frequently selected features that could discriminate between high-risk and low-risk regions within the training set from patient groups. mRMR is a feature selection method that selects the most relevant features for prediction by maximizing the mutual information (MI) between the selected features and the PCa labels for different patient groups, while minimizing the mutual information (MI) between each feature and the other in order to increase robustness of the final prediction model. In this example, a reduced feature vector was formed for further processing with only the most relevant features that exhibited statistically significant differential expression between the different groups retained.

Embodiments may employ mpMRI-derived peritumoral radiomic features to train a machine learning classifier to stratify or predict PCa risk as defined by D'Amico. Based on D'Amico classification, lesions were segregated into three groups of risk: low-risk, intermediate-risk, and high-risk. The multi-institutional patient cohort was divided into two subsets where the first (Group 1: 210 lesions from 150 patients, illustrated at 620) was used for training and the second (Group 2: 210 lesions from 141 patients, illustrated at 630) was only used for validation. Each T2w MRI was corrected for inherent scanner variability using a drift correction technique. Studies (e.g., MRI imagery) acquired using an endo-rectal coil were bias field corrected.

In this example, mRMR was used to identify and rank a set of ten features that could discriminate between high-risk and low-risk regions within the training set from patient groups. The top ten two-dimensional (2D) radiomic features determined by mRMR were extracted within PCa regions from T2W MRI imagery and ADC maps. A quadratic discriminant analysis (QDA) machine-learning classifier in conjunction with feature selection was trained using Group 1, illustrated at 620, then was used to identify the risk categories on bpMRI on the independent validation subset (Group 2, illustrated at 630). Multi-lesion cases were ensured to be on only one subset i.e. lesions from a patient were strictly either used for training or validation.

Figure 9:
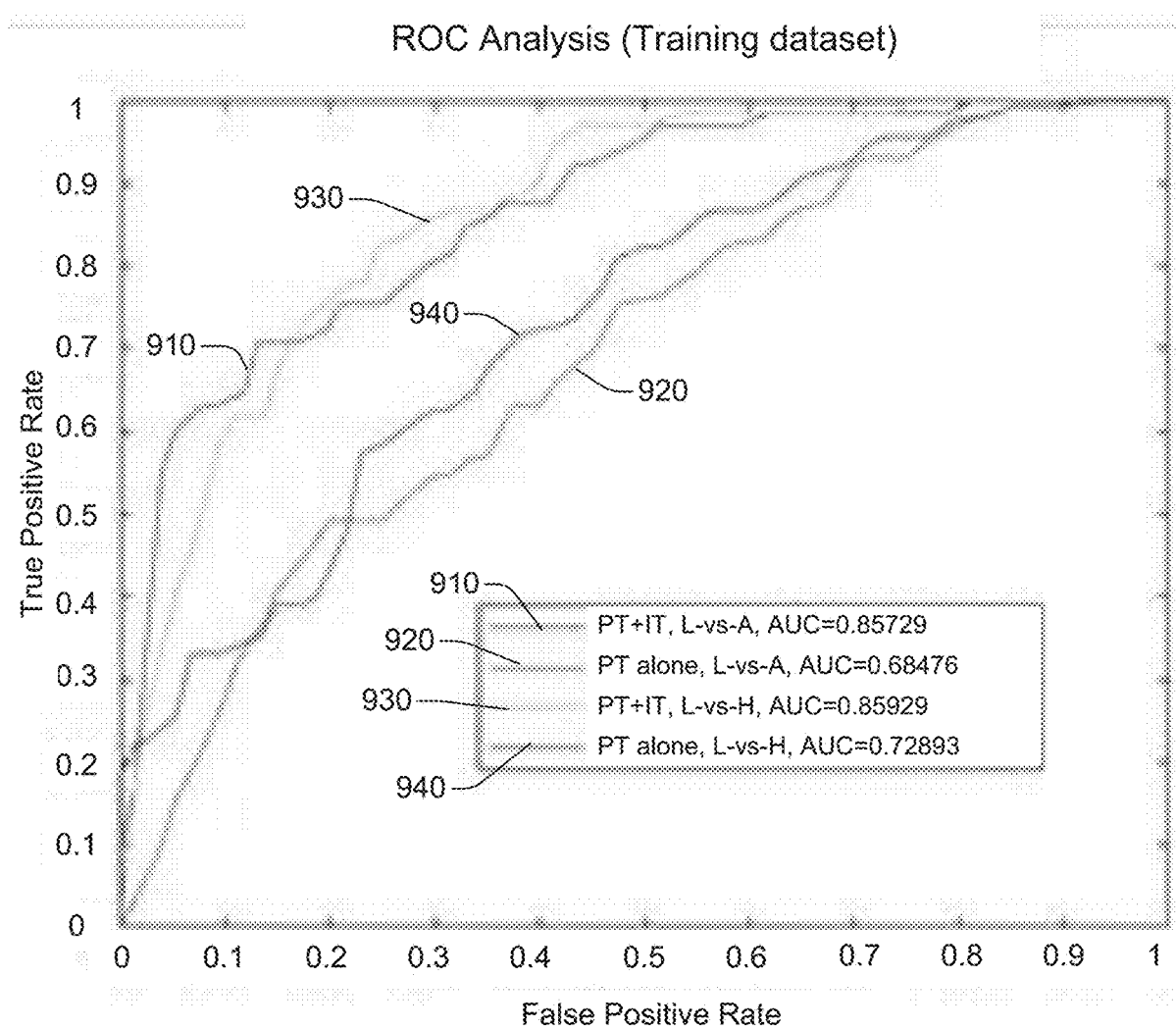
FIG. 9 illustrates a graph showing Area Under the Receiver Operating Characteristic Curves (AUC) on a training set according to various embodiments discussed herein.
Figure 10:
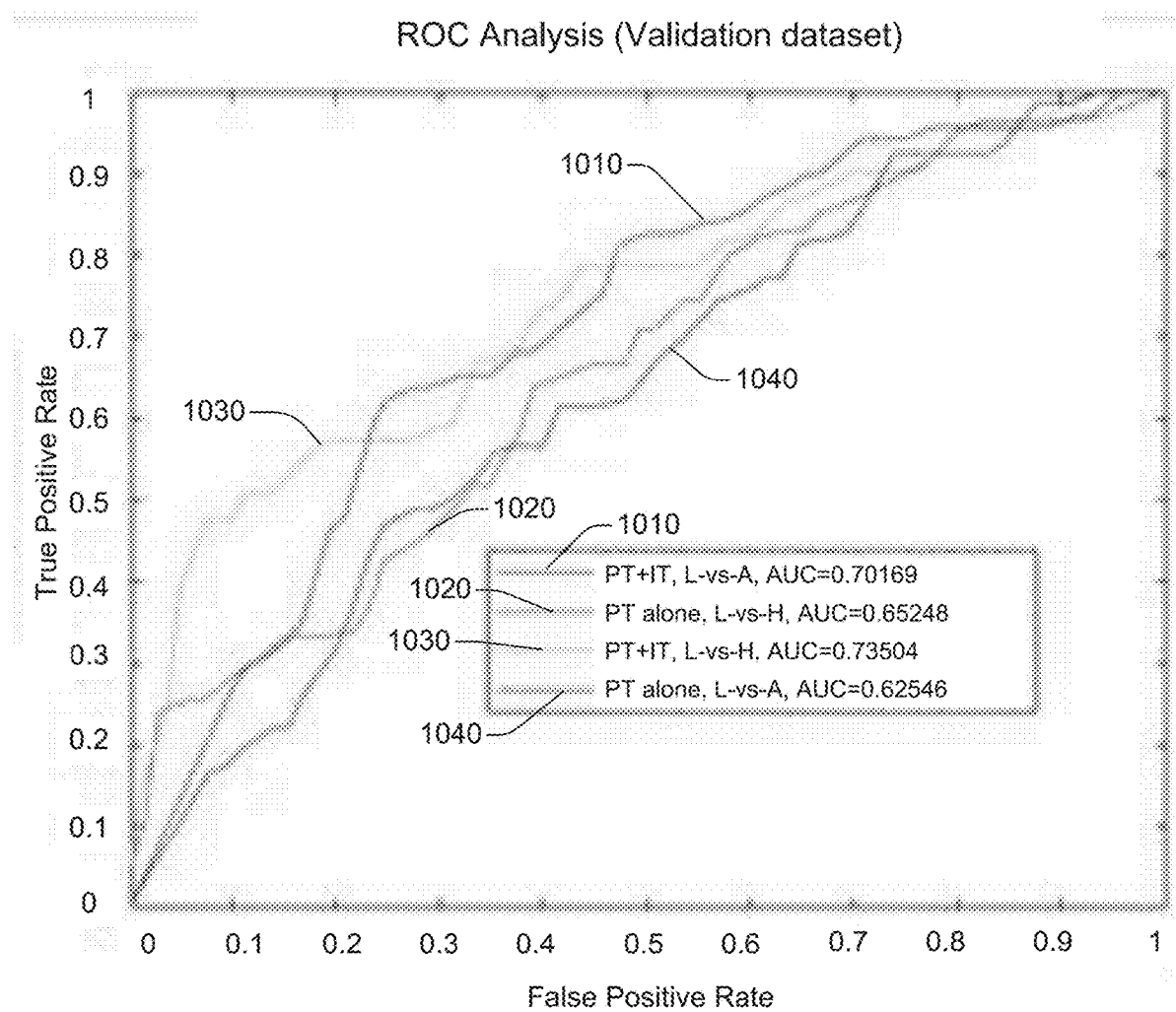
FIG. 10 illustrates a graph showing Area Under the Receiver Operating Characteristic Curves (AUC) on a testing set according to various embodiments discussed herein.

FIG. 11 illustrates a table 1100 that lists the most relevant peri-tumoral radiomic features selected by mRMR from bpMRI imagery in this example using the training cohort illustrated at 620 (n=210 lesions) to stratify PCa risk in Low-versus-High (L-vs-H), and Low-versus-All (L-vs-A) settings. Gabor, Laws, and Haralick features from the 3-6 mm and 9-12 mm rings were found to be the most predictive PT features in the bi-parametric setting. FIGS. 9 and 10 illustrate the ROC analysis results. The training cohort yielded areas under the ROC curve (AUCs) of 0.66, 0.68, and 0.72 for T2W, ADC, and T2W+ADC, respectively, in the L-vs-H settings using only peritumoral radiomic features. In the L-vs-A setting, AUCs were 0.63, 0.64, and 0.68, for T2W, ADC, and T2W+ADC, respectively. FIG. 9 illustrates, at 920 an ROC curve for peritumoral radiomic features alone in the L-vs-A setting using the training dataset. FIG. 9 illustrates, at 940 an ROC curve for peritumoral radiomic features alone in the L-vs-H setting using the training dataset.

For the validation cohort illustrated at 630 (n=210), in the L-vs-H setting, ROC analysis resulted in AUCs of 0.64, 0.65, and 0.65 for T2W, ADC, and T2W+ADC, respectively. Similarly, in the L-vs-A setting, AUCs were 0.60, 0.61, and 0.63 for T2W and ADC, and T2W+ADC, respectively. FIG. 10 illustrates, at 1020 an ROC curve for peritumoral radiomic features alone in the L-vs-H setting using the test dataset. FIG. 10 illustrates, at 1040 and ROC curve for peritumoral radiomic features alone in the L-vs-A setting using the test dataset.

Embodiments may employ mpMRI-derived intra-tumoral and peritumoral radiomic features to train a machine learning classifier to stratify PCa risk as defined by D'Amico. In this example, 600 more radiomic features (300 for each MRI protocol) were extracted from within the tumoral regions. This facilitates evaluating the effect of combining intratumoral and peritumoral features in stratifying PCa risk. After extraction of the intratumoral and peritumoral feature sets, feature selection was performed to identify the best combination of discriminative features. A different QDA classifier was trained in conjunction with the identified optimal feature set, followed by an ROC analysis.

Figure 12:
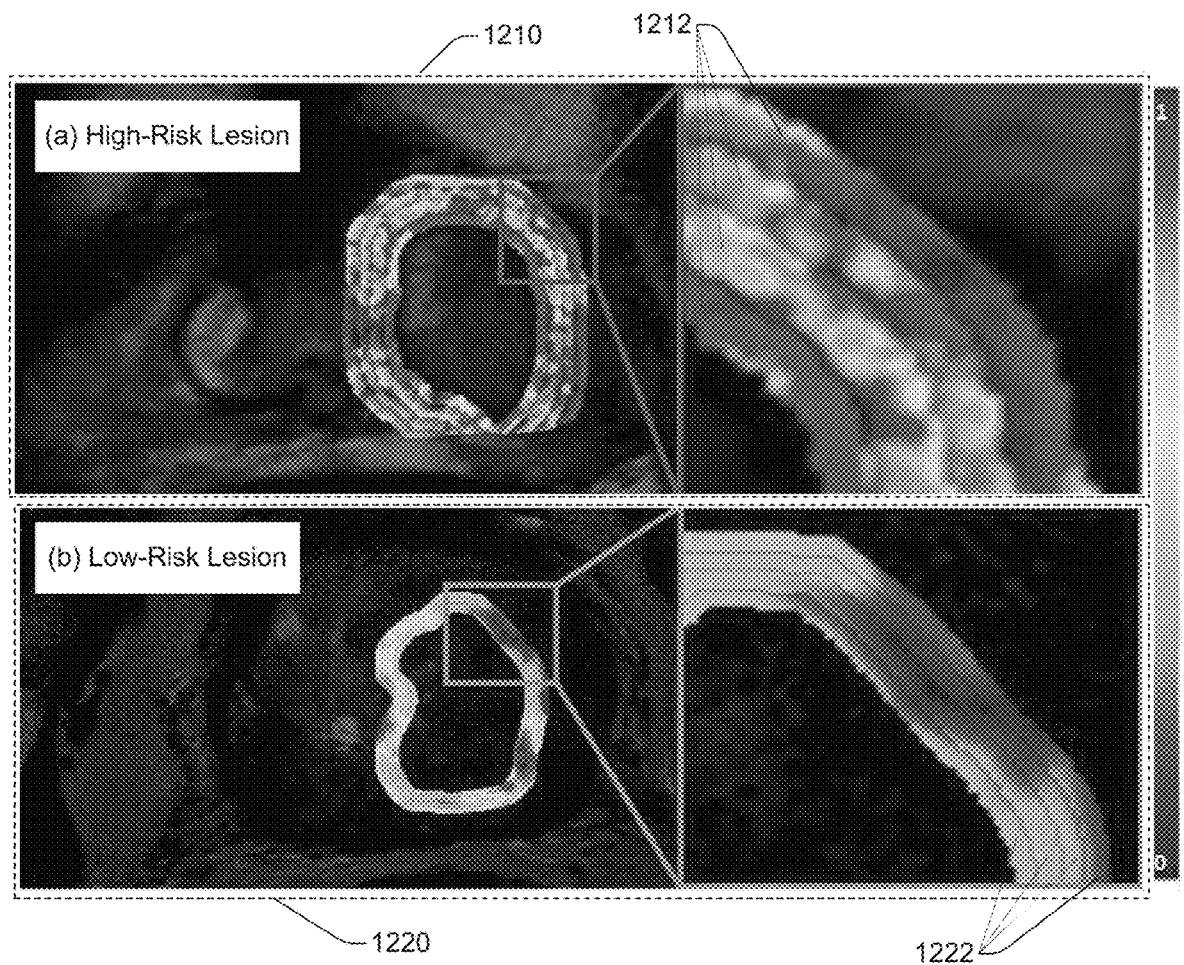
FIG. 12 illustrates T2W MRI scans of a high-risk PCa lesion and a low-risk PCa lesion with corresponding co-occurrence of local anisotropic gradient orientations (CoLIAGe) entropy heatmaps from peritumoral (0-12 mm) regions.

Embodiments that include a set of radiomic features that includes PT radiomic features and IT radiomic features improve PCa risk stratification results by up to 25% compared to PT features alone. FIG. 13 illustrates a table 1300 that describes the top ten combined (IT and PT) radiomic features found to be the most predictive of PCa risk. FIG. 12 illustrates example top radiomic features from low-risk lesion 1220 and high-risk lesion 1210 with their respective peritumoral feature rings 1222 and 1212. For the training dataset, the most discriminative set of IT and PT bpMRI features resulted in AUCs of 0.859 and 0.857 for the L-vs-H and L-vs-A classifications, respectively. FIG. 9 illustrates, at 910 an ROC curve for peritumoral radiomic features and intratumoral radiomic features in the L-vs-A setting using the training dataset. FIG. 9 illustrates, at 930 an ROC curve for peritumoral radiomic features and intratumoral radiomic features in the L-vs-H setting using the training dataset. Similarly, for the validation dataset, AUCs were 0.701 and 0.735 for the L-vs-H and L-vs-A settings, respectively. FIG. 10 illustrates, at 1010 an ROC curve for peritumoral radiomic features and intratumoral radiomic features in the L-vs-A setting using the test dataset. FIG. 10 illustrates, at 1030 an ROC curve for peritumoral radiomic features and intratumoral radiomic features in the L-vs-H setting using the test dataset.

Embodiments improve on existing approaches to predicting PCa progression risk, including stratifying PCa risk according to D'Amico, and PIRADS. For example, embodiments using mpMRI derived radiomic features were compared to PIRADS v2 assessment for PCa risk stratification. On bpMRI, based on PIRADS scores, lesions of the validation cohort (n=210) were segregated into 2 groups of low (PIRADS 1-2) and high (PIRADS 3-5) clinical significance. In this example, first was investigated the capability of PIRADS to stratify PCa risk by means of creating a confusion matrix between D'Amico and PIRADS. Then, results from the QDA machine learning classifier trained with the combined (IT+PT) set of ten radiomic features already extracted were compared to PIRADS.

FIG. 14 illustrates a table 1400 that shows risk stratification using PIRADS and predictions from embodiments using a QDA machine learning classifier using IT and PT radiomic features on the validation cohort according to embodiments described herein. Out of two-hundred and ten (210) lesions, PIRADS correctly identified 48 high-risk and 37 low-risk lesions, while the radiomic model according to embodiments described herein identified 39 high-risk and 79 low-risk lesions. High PIRADS (4, 5) is significantly associated with high risk lesions, however the associations with low risk lesions remain ambiguous, and thus existing approaches that employ PIRADS may be sub-optimal in a clinical setting. In contrast, embodiments described herein that employ a machine learning classifier trained on intratumoral and peritumoral radiomic features as described herein are significantly more accurate than PIRADS in predicting low-risk lesions and comparable to PIRADS in identifying the high risk lesions. Improved identification of patients at low risk of progression may enable identifying patients who could be potential candidates for active surveillance and has significant clinical benefit.

Embodiments demonstrate the relationship or association between peritumoral radiomic features and histopathological attributes of PCa tissue. In one example, associations between peritumoral radiomic features and corresponding histopathology were evaluated to obtain a morphological understanding of the discriminating set of radiomic features. Whole mount prostate specimens obtained from patients belonging to each of low, intermediate, and high risk categories were stained with hematoxylin and eosin (H&E), sliced, and digitized at 20× to obtain whole mount pathology (WMP). Correspondences between mpMRI and WMP were obtained based on anatomical landmarks and PCa ROIs were annotated on mpMRI by an experienced radiologist using WMP as a reference. An experienced pathologist delineated ROIs on digitized WMP. Peritumoral ROIs were obtained on mpMRI and WMP by computing annular rings within the prostate extending beyond the tumor ROI as previously described herein. Deep learning-based tissue segmentation approaches were used to compute epithelium, lumen and stromal density within the peritumoral ROIs on whole mount pathology.

Density of stroma in the peritumoral ring just outside the tumor (0-3 mm) was lower in high-risk PCa compared to low risk and intermediate risk. Density of epithelium in the peritumoral ring just outside the tumor (0-3 mm) was higher in high-risk PCa compared to low risk and intermediate risk. The amount of lumen was fairly constant across all risk categories. Moving away from the tumor, the density of stroma increased for all risk categories, however, the rate of increase was greater in low and intermediate-risk lesions compared to high-risk lesions.

Embodiments demonstrate a histological rationale for PT radiomics by correlating them with tissue compartment density. For example, in addition to radiomic features derived from within the tumor, peritumoral radiomic features were found to be able to distinguish PCa of the different D'Amico risk categories. Specifically, Haralick features (extracted from 0-3 mm and 6-9 mm annular rings) and Law's features (extracted from a 9-12 mm annular ring) were observed to be over expressed and under expressed respectively in high risk lesions compared to low and intermediate risk lesions. Haralick features characterized underlying heterogeneity of mpMRI signal by quantifying spatial intensity relationships. Over-expression of peritumoral Haralick features in 0-3 mm and 6-9 mm annular rings for high-risk indicates increased heterogeneity and was reflected in terms of higher epithelial density just surrounding the tumor. The epithelial segmentation algorithm employed in this example included epithelial nuclei along with lymphocytes. Laws features characterizing edges in the horizontal and vertical directions were observed to be under expressed in high-risk patients, indicating that edge orientations were along different directions. This again suggests heterogeneity similar to that captured by Haralick features.

Figure 16:
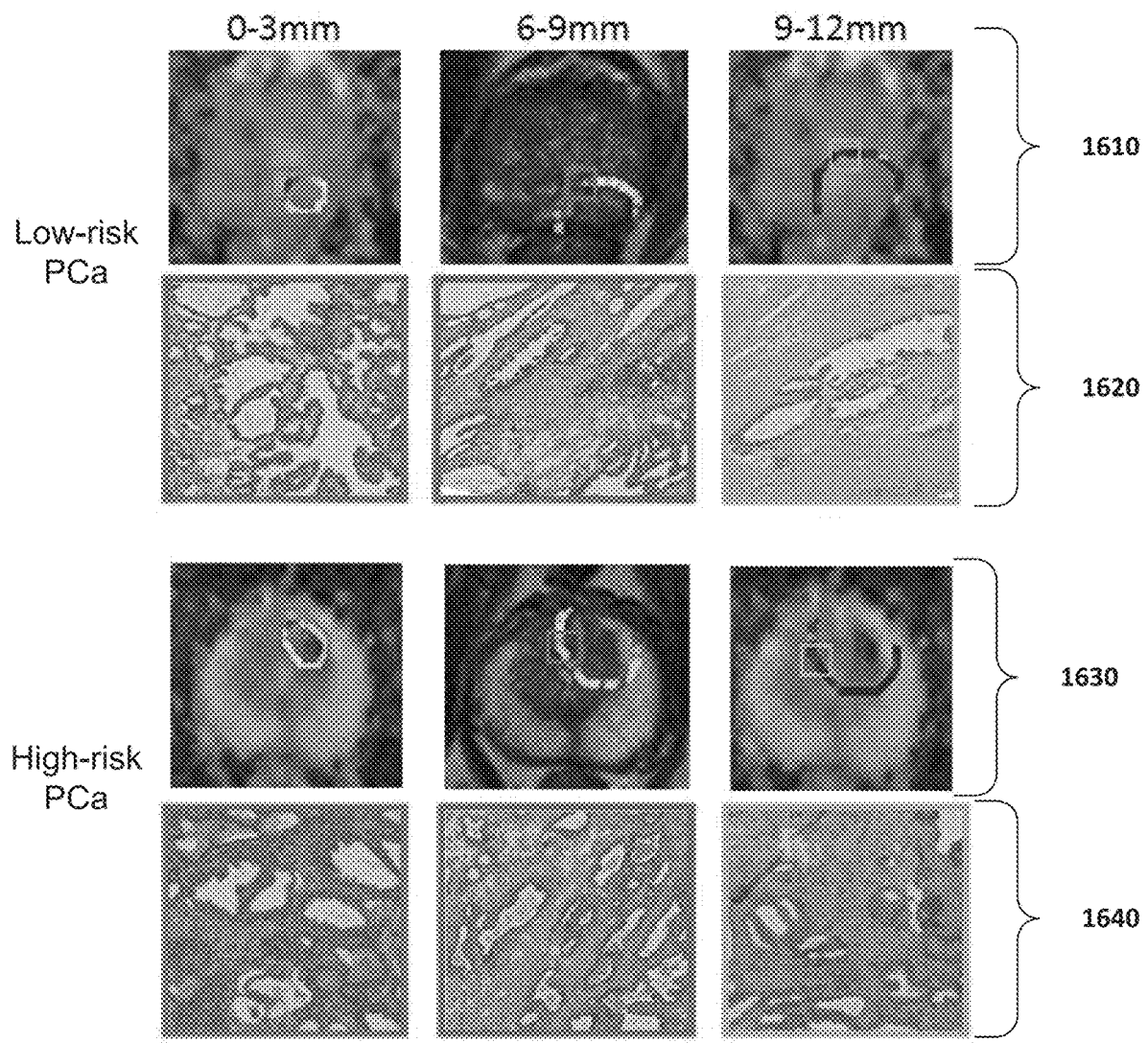
FIG. 16 illustrates radiomic features in the peritumoral region (0-3 mm, 6-9 mm, 9-12 mm) overlaid on T2W MRI and apparent diffusion co-efficient (ADC) maps, and epithelium, stroma and lumen compartment segmentations from corresponding regions overlaid on histopathology.

FIG. 16 illustrates radiomic features in the peritumoral region overlaid on T2W MRI and ADC. In row 1610 and row 1630, radiomic features in the peritumoral region (0-3, 6-9, 9-12 mm) overlaid on T2W MRI and ADC are illustrated. In row 1620 and row 1640, epithelium, stroma and lumen compartment segmentations from corresponding regions overlaid on histopathology are illustrated. Epithelial density is greater in high risk lesions compared to low risk lesions and converse with stroma. Stromal content decreases moving away from the lesion.

As demonstrated by the example embodiments, various embodiments can facilitate prediction of PCa progression risk based on radiomic features including tumoral radiomic features and peritumoral radiomic features, extracted from bpMRI images. The ability to identify or stratify patients into PCa risk categories based on tumoral radiomic features and peritumoral radiomic features extracted from bpMRI images using a machine learning classifier trained according to embodiments described herein can facilitate improving the utility of bpMRI as a non-invasive PCa risk assessment tool for identifying candidate patients for active surveillance.

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods or operations 100, 200, 300, 2000, or any other methods or operations described herein. While executable instructions associated with the listed methods are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein related to prediction of PCa progression risk are based on intratumoral and peritumoral radiomic features that are not perceivable by the human eye, and their computation cannot be practically performed in the human mind. A machine learning classifier as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then used and applied to create desired results more accurately, more consistently, and with greater reliability than existing approaches, thereby producing the technical effect of improving the performance of the machine, computer, or system with which embodiments are implemented.

Figure 17:
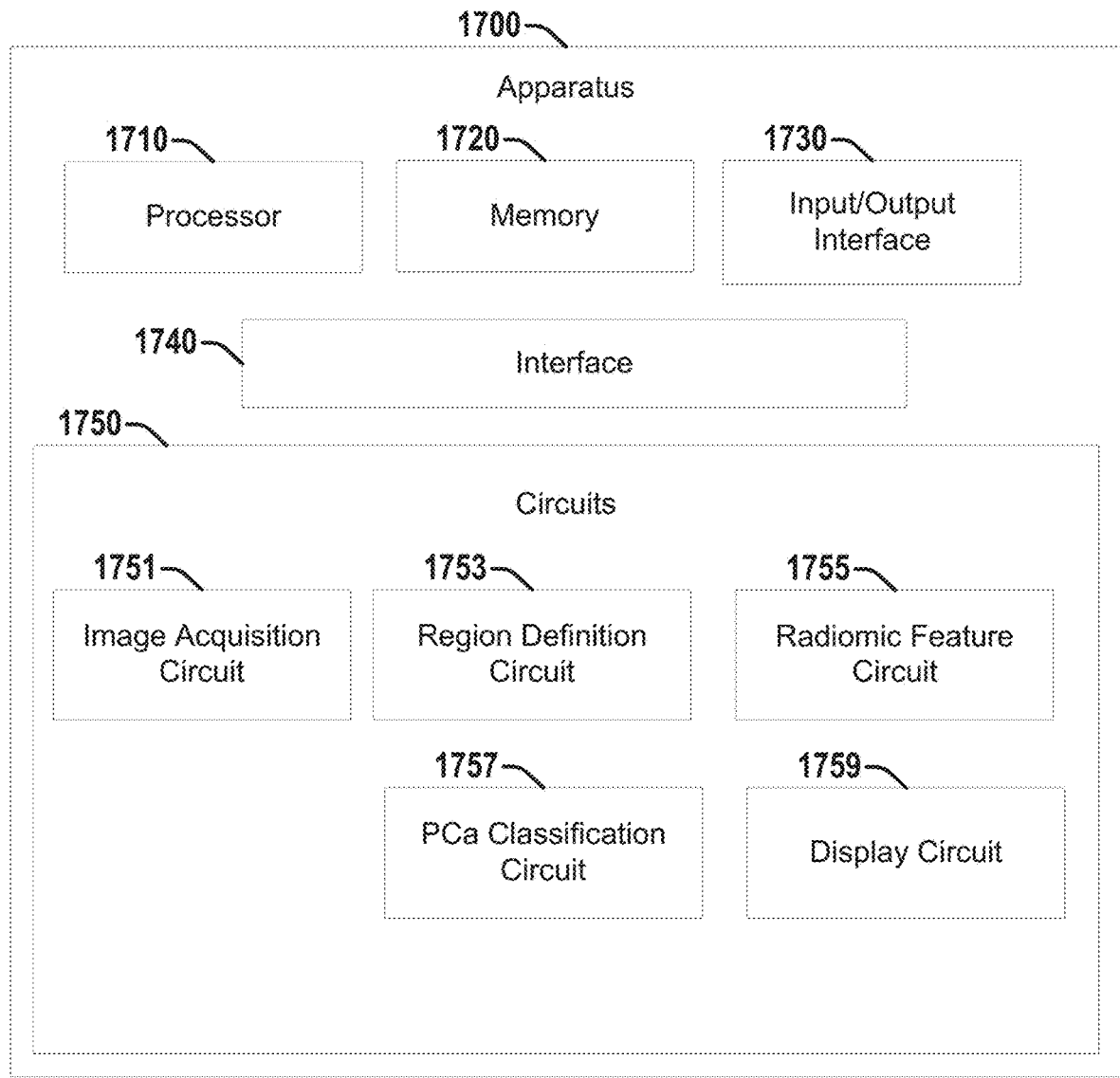
FIG. 17 illustrates a diagram of an example apparatus that can facilitate classifying an ROI demonstrating PCa according to various embodiments discussed herein.

FIG. 17 illustrates an example apparatus 1700 that can facilitate predicting PCa progression risk based on radiomic features extracted from MRI imagery, according to various embodiments discussed herein. Apparatus 1700 may be configured to perform various techniques, operations, or methods discussed herein, for example, training a machine learning classifier (e.g., quadratic discriminant analysis classifier, support vector machine, etc.) based on training data to determine probability of PCa progression risk based on radiomic features extracted from MRI imagery, or employing such a trained machine learning classifier to generate a classification of PCa progression risk (e.g., low-risk, intermediate risk, high-risk) based on tumoral or peritumoral radiomic features extracted from an MRI image (e.g., mpMRI, bpMRI) of a patient demonstrating PCa. In one embodiment, apparatus 1700 includes a processor 1710, and a memory 1720. Processor 1710 may, in various embodiments, include circuitry such as, but not limited to, one or more single-core or multi-core processors. Processor 1710 may include any combination of general-purpose processors and dedicated processors (e.g., graphics processors, application processors, etc.). The processor(s) can be coupled with and/or can comprise memory (e.g., memory 1720) or storage and can be configured to execute instructions stored in the memory 1720 or storage to enable various apparatus, applications, or operating systems to perform operations and/or methods discussed herein.

Memory 1720 is configured to store a bi-parametric magnetic resonance imaging (bpMRI) image associated with a patient, where the image includes a region of interest (ROI) demonstrating prostate cancer (PCa) pathology. The bpMRI image has a plurality of pixels, a pixel having an intensity. The bpMRI image may include a plurality of voxels, a voxel having an intensity. The bpMRI image includes a T2W MRI image and an apparent diffusion coefficient (ADC) map. In some embodiments, memory 1720 can store a training set of images (e.g., comprising bpMRI images showing radiomic features, along with a known risk of PCa progression) for training a classifier (e.g., QDA classifier, etc.) to determine a probability of risk of PCa progression, while in the same or other embodiments, memory 1720 can store a radiological image of a patient for whom a prediction of PCa progression risk is to be determined. Memory 1720 can be further configured to store one or more clinical features or other data associated with the patient of the bpMRI image.

Apparatus 1700 also includes an input/output (I/O) interface 1730; a set of circuits 1750; and an interface 1740 that connects the processor 1710, the memory 1720, the I/O interface 1730, and the set of circuits 1750. I/O interface 1730 may be configured to transfer data between memory 1720, processor 1710, circuits 1750, and external devices, for example, a medical imaging device such as an MRI system or apparatus.

The set of circuits 1750 includes image acquisition circuit 1751, region definition circuit 1753, radiomic feature circuit 1755, PCa classification circuit 1757, and display circuit 1759.

Image acquisition circuit 1751 is configured to access the bpMRI image. Accessing the bpMRI image may include accessing the bpMRI image stored in memory 1720. In another embodiment accessing the bpMRI image may include acquiring electronic data, reading from a computer file, receiving a computer file, reading from a computer memory, or other computerized activity not practically performed in the human mind.

Region definition circuit 1753 is configured to segment a tumoral region represented in the bpMRI image. Segmenting the tumoral region includes defining a tumoral boundary. In one embodiment, region definition circuit 1753 is configured to automatically segment the tumoral region using a watershed segmentation technique, a region growing or active contour technique, or a convolutional neural network (CNN) approach. Region definition circuit 1753 is also configured to define a peritumoral region based on the tumoral boundary according to techniques described herein. The peritumoral region includes a plurality of annular rings.

Radiomic feature circuit 1755 is configured to extract a first set of radiomic features from the bpMRI image. The first set of radiomic features includes at least one radiomic feature extracted from the peritumoral region, and at least one, different radiomic feature extracted from the tumoral region. In one embodiment, the first set of radiomic features includes an intratumoral Laws (15) feature extracted from the T2W image, an intratumoral Canny feature extracted from the T2W image, a peritumoral co-occurrence of local anisotropic gradient orientations (CoLlAGe) entropy feature extracted from the ADC map, an intratumoral Laws (11) feature extracted from the ADC image, an intratumoral Haralick (entropy) feature extracted from the ADC map, an intratumoral CoLlAGe feature extracted from the ADC map, a peritumoral Haralick (info measure 1) feature extracted from the T2W image, a peritumoral Laws (17) feature extracted from the ADC map, an intratumoral Haralick (info measure 2) feature extracted from the T2W image, and an intratumoral Haralick (info measure 2) feature extracted from the ADC map.

PCa classification circuit 1757 is configured to compute a first probability that the patient associated with the ROI has a low-risk of PCa progression, or a high-risk of PCa progression. PCa classification circuit 1757 computes the first probability based on the first set of radiomic features. PCa classification circuit 1757 is also configured to generate a first classification of the patient as having low-risk of PCa progression, or a high-risk of PCa progression based, at least in part, on the first probability.

Display circuit 1759 is configured to display the first classification. In various embodiments, the classification may include one or more of a most likely outcome (e.g., as determined based on the radiomic features) such as low-risk of PCa progression, intermediate risk of PCa progression, or high-risk of PCa progression; a probability or confidence associated with a most likely outcome; and/or associated probabilities/confidences associated with each of a plurality of outcomes.

In one embodiment, radiomic feature circuit 1755 is further configured to extract a second set of radiomic features from the bpMRI image. The second set of radiomic features includes at least one radiomic feature extracted from the peritumoral region, and at least one, different radiomic feature extracted from the tumoral region. In one embodiment, the second set of radiomic features includes an intratumoral Gabor (6 Hz, 2.0 rad) feature extracted from the T2W image, a peritumoral Gabor (6 Hz, 2.8 rad) feature extracted from the T2W image, a peritumoral Haralick (momentum sum) feature extracted from the ADC map, an intratumoral Gabor (6 Hz, 1.8 rad) feature extracted from the ADC map, a mean filter (3 pixel by 3 pixel window) response feature extracted from the peritumoral region of the T2W image, an intratumoral Gabor (2.5 Hz, 0.4 rad) feature extracted from the T2W image, an intratumoral Gabor (3 Hz, 0.4 rad) feature extracted from the T2W image, an intratumoral Gabor (3.5 Hz, 0.4 rad) feature extracted from the T2W image, an intratumoral Gabor (5 Hz, 1.6 rad) feature extracted from the ADC map, and an intratumoral Gabor (6 Hz, 1.6 rad) feature extracted from the ADC map. In another embodiment, the first set of radiomic features or the second set of radiomic features may include numbers of radiomic features, or different radiomic features.

In one embodiment, PCa classification circuit 1757 is further configured to compute a second probability that the patient associated with the ROI has a low-risk of PCa progression, or a high-risk of PCa progression or intermediate-risk of PCa progression, based on the second set of radiomic features. In this embodiment, PCa classification circuit 1757 is further configured to generate a second classification of the patient as having low-risk of PCa progression, or a high-risk or intermediate-risk of PCa progression based, at least in part, on the second probability. In this embodiment, display circuit 1759 is further configured to display the second classification.

In another embodiment, radiomic feature circuit 1755 is further configured to compute first order statistics associated with each member of the first set of radiomic features or the second set of radiomic features. In this embodiment, PCa classification circuit 1757 is configured to compute the first probability based on the first set of radiomic features and/or the first order statistics, or compute the second probability based on the second set of radiomic features and/or the first order statistics.

In one embodiment, PCa classification circuit 1757 is configured as a quadratic discriminant analysis (QDA) classifier. In another embodiment, PCa classification circuit 1757 is configured as another, different type of machine learning classifier. For example, PCa classification circuit 1757 may be configured as a support vector machine (SVM) classifier, a linear discriminant analysis (LDA) classifier, a random forests (RF) classifier, or a deep learning classifier, including a convolutional neural network (CNN).

Figure 18:
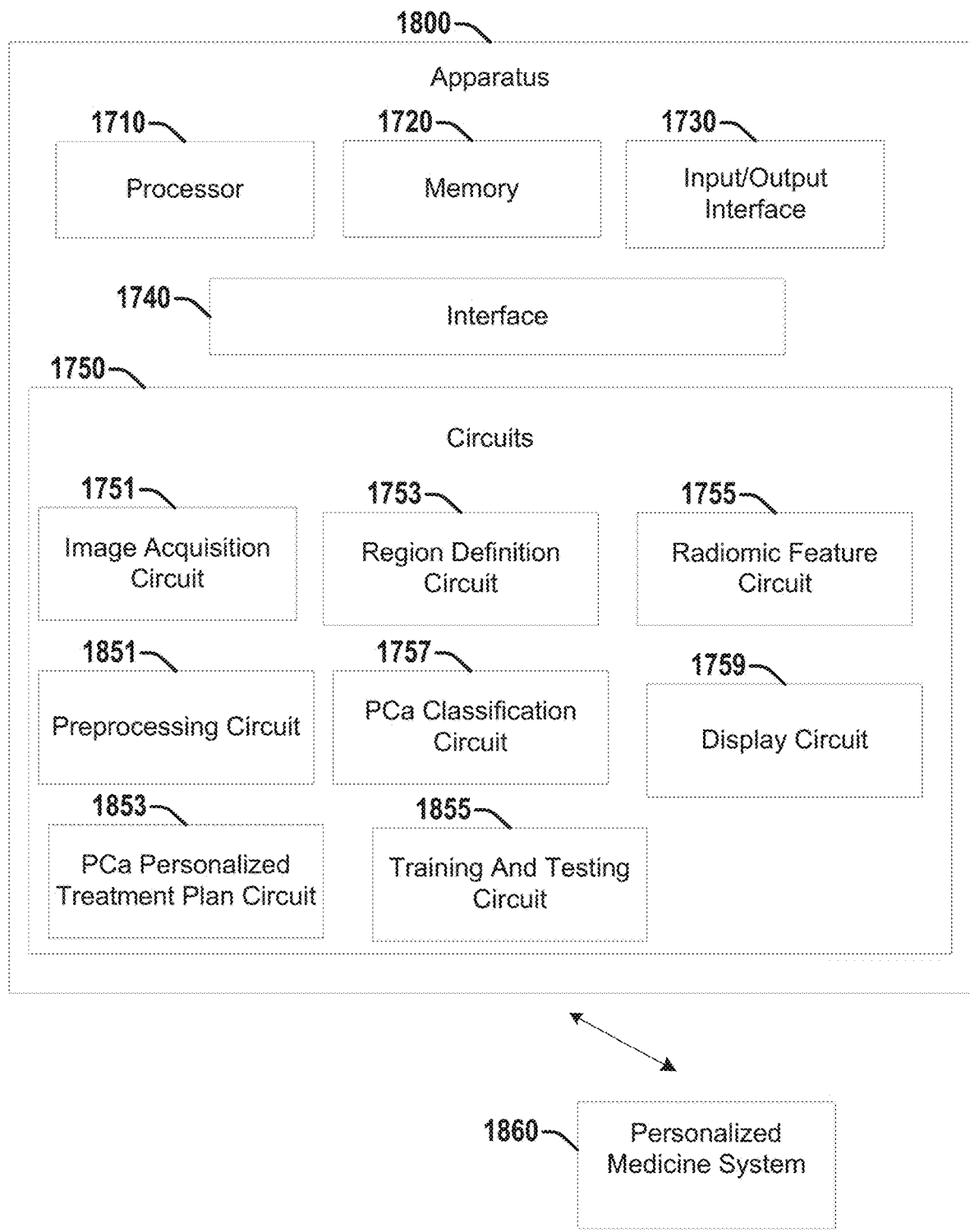
FIG. 18 illustrates a diagram of an example apparatus that can facilitate classifying an ROI demonstrating PCa according to various embodiments discussed herein.

FIG. 18 illustrates an apparatus 1800 that is similar to apparatus 1700 but that includes additional elements and details. In one embodiment of apparatus 1800, the set of circuits 1750 further includes a pre-processing circuit 1851 configured to preprocess the bpMRI image. Pre-processing circuit 1851 is configured to preprocess the bpMRI image by: resampling the image to a pixel size of 0.5×0.5 mm$^2$;

cropping the ROI with 2 mm padding along the x axis and y axis; interpolating the image to a 3 mm slice thickness; verifying that the T2W image and ADC map represent the same three dimensional (3D) space; and correcting scanner variability using a drift correction approach. In one embodiment, pre-processing circuit 1851 is configured to preprocess the bpMRI image by any of or any combination of: resampling the image to a first pixel size (e.g., 0.5×0.5 mm$^2$, 1×1 mm$^2$); cropping the ROI with threshold level (e.g., 1 mm, 2 mm, 3 mm, 4 mm) of padding along the x axis and y axis; interpolating the image to a first slice thickness (e.g., 2 cm, 3 cm, 4 cm); verifying that the T2W image and ADC map represent the same three dimensional (3D) space; or correcting scanner variability using a drift correction approach. In another embodiment, other values may be employed for the pre-processing parameters (e.g., pixel size, padding, slice thickness, etc.).

In one embodiment of apparatus 1800, the set of circuits 1750 further includes a PCa personalized treatment plan circuit 1853 configured to generate a personalized treatment plan based, at least in part, on the classification. PCa personalized treatment plan circuit 1853 may be configured to generate a personalized treatment plan based, at least in part, on a classification obtained from PCa classification circuit 1757 or display circuit 1759. PCa personalized treatment plan circuit 1853 may be configured to generate a personalized treatment plan for the patient of whom the bpMRI image was acquired based, at least in part, on the classification derived therefrom. Defining a personalized treatment plan facilitates delivering a particular treatment that will be therapeutically active to the patient, while minimizing negative or adverse effects experienced by the patient. For example, the personalized treatment plan may suggest a surgical treatment, may suggest a pharmaceutical agent dosage or schedule, and/or other treatments. Generating a personalized treatment plan based on a more accurate prediction of PCa progression risk facilitates more efficient delivery of costly therapeutic or surgical treatments to patients more likely to benefit from such treatments. For example, the personalized treatment plan may suggest a first surgical treatment, may suggest a first pharmaceutical agent dosage or schedule, and/or other treatments for a patient classified as low-risk of PCa progression, or may suggest a second, different surgical treatment or second, different pharmaceutical agent dosage or schedule or treatments for a patient classified as high-risk.

In this embodiment, display circuit 1759 is further configured to display the personalized treatment plan.

In one embodiment of apparatus 1800, the set of circuits 1750 further includes a training and testing circuit 1855. Training and testing circuit 1855 is configured to train PCa classification circuit 1757 on a multi-institutional cohort; and optionally test PCa classification circuit 1757 on a multi-institutional testing cohort.

In various embodiments, PCa classification circuit 1757 can receive one or more radiomic features or values (including, for example, first order statistical values) for the one or more radiomic feature extracted from a bpMRI image from radiomic feature circuit 1755. In some embodiments, the received features or values of the features can correspond to an image of a training dataset, and PCa classification circuit 1757 can be trained based on the values and a known risk of PCa progression associated with the image. In the same or other embodiments, the features or received values of the features can correspond to an image of a testing dataset or of a patient for whom a prediction of PCa progression risk is to be generated, and PCa classification circuit 1757 can generate a prognosis based on the radiomic feature(s) or received values.

In one embodiment, apparatus 1800 further includes personalized medicine system or device 1860. Apparatus 1800 may be configured to provide the first probability, the second probability, the first classification, the second classification, a personalized treatment plan, or other data to personalized medicine device 1860. Personalized medicine device 1860 may be, for example, a computer assisted diagnosis (CADx) system or other type of personalized medicine device that can be used to facilitate the prediction of disease progression risk. In one embodiment, PCa personalized treatment plan circuit 1853 can control personalized medicine device 1860 to display the first probability, the second probability, the first classification, the second classification, a personalized treatment plan, or other data to on a computer monitor, a smartphone display, a tablet display, or other displays.

Figure 19:
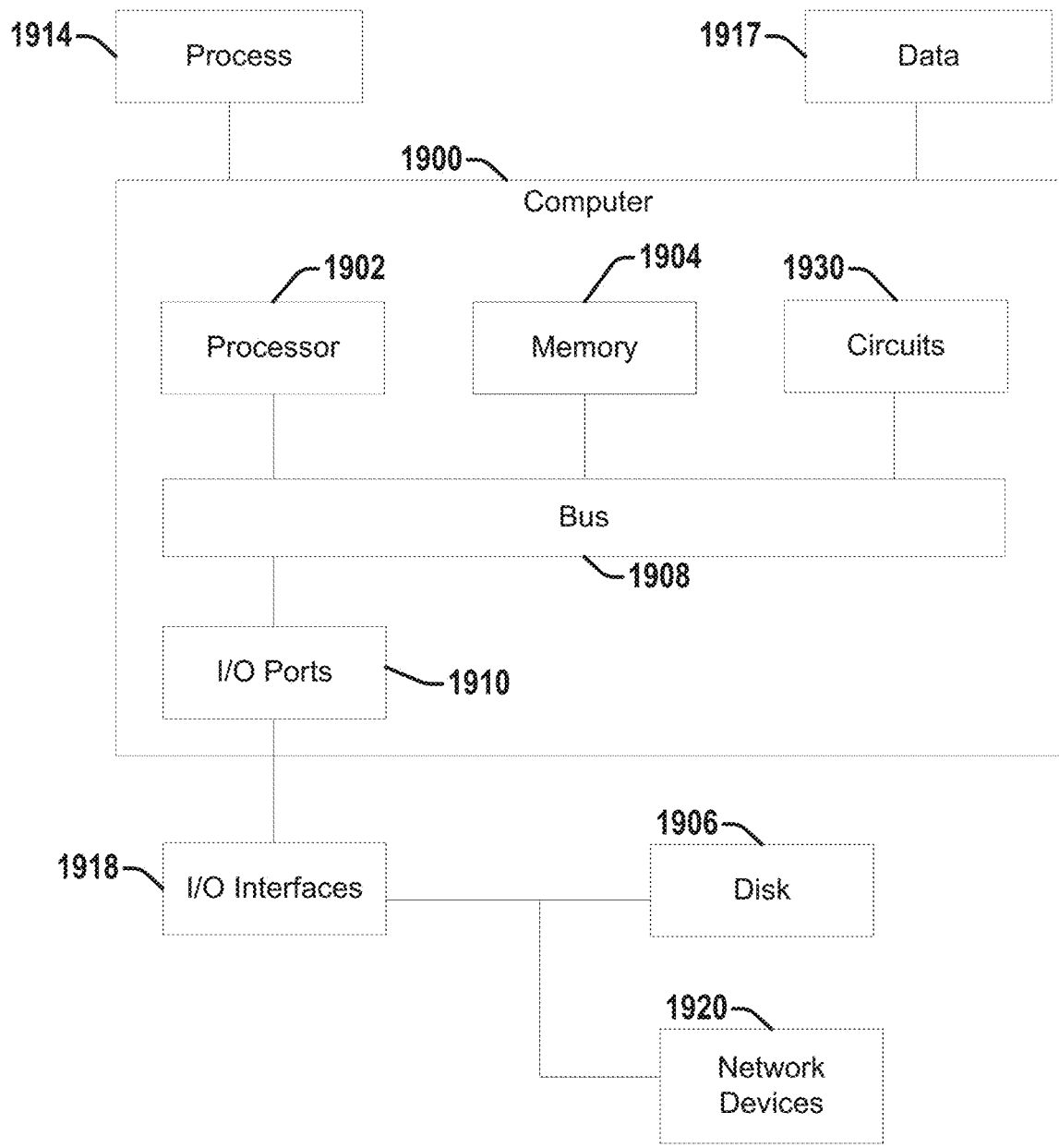
FIG. 19 illustrates a diagram of an example computer in which embodiments described herein may be implemented.

FIG. 19 illustrates an example computer 1900 in which example methods illustrated herein can operate and in which example methods, apparatus, circuits, operations, or logics may be implemented. In different examples, computer 1900 may be part of a PCa progression risk prediction system or apparatus, a PCa tumor classification system or apparatus, a CADx system, an MRI system, a CT system, a digital whole slide scanner, or a personalized medicine system, or may be operably connectable to PCa progression risk prediction system or apparatus, a PCa tumor classification system or apparatus, a CADx system, an MRI system, a CT system, a digital whole slide scanner, or a personalized medicine system.

Computer 1900 includes a processor 1902, a memory 1904, and input/output (I/O) ports 1910 operably connected by a bus 1908. In one example, computer 1900 may include a set of logics or circuits 1930 that perform operations for or a method of predicting PCa progression risk, or classifying PCa tumors on MRI imagery, including by using a machine learning classifier. Thus, the set of circuits 1930, whether implemented in computer 1900 as hardware, firmware, software, and/or a combination thereof may provide means (e.g., hardware, firmware, circuits) for predicting PCa progression risk, or classifying PCa tumors on MRI imagery. In different examples, the set of circuits 1930 may be permanently and/or removably attached to computer 1900.

Processor 1902 can be a variety of various processors including dual microprocessor and other multi-processor architectures. Processor 1902 may be configured to perform steps of methods claimed and described herein. Memory 1904 can include volatile memory and/or non-volatile memory. A disk 1906 may be operably connected to computer 1900 via, for example, an input/output interface (e.g., card, device) 1918 and an input/output port 1910. Disk 1906 may include, but is not limited to, devices like a magnetic disk drive, a tape drive, a Zip drive, a flash memory card, or a memory stick. Furthermore, disk 1906 may include optical drives like a CD-ROM or a digital video ROM drive (DVD ROM). Memory 1904 can store processes 1914 or data 1917, for example. Data 1917 may, in one embodiment, include digitized radiological images, including MRI images of tissue demonstrating PCa. Disk 1906 or memory 1904 can store an operating system that controls and allocates resources of computer 1900.

Bus 1908 can be a single internal bus interconnect architecture or other bus or mesh architectures. While a single bus is illustrated, it is to be appreciated that computer 1900 may communicate with various devices, circuits, logics, and peripherals using other buses that are not illustrated (e.g., PCIE, SATA, Infiniband, 1394, USB, Ethernet).

Computer 1900 may interact with input/output devices via I/O interfaces 1918 and input/output ports 1910. Input/output devices can include, but are not limited to, MRI systems, CT systems, digital whole slide scanners, an optical microscope, a keyboard, a microphone, a pointing and selection device, cameras, video cards, displays, disk 1906, network devices 1920, or other devices. Input/output ports 1910 can include but are not limited to, serial ports, parallel ports, or USB ports.

Computer 1900 may operate in a network environment and thus may be connected to network devices 1920 via I/O interfaces 1218 or I/O ports 1210. Through the network devices 1920, computer 1900 may interact with a network. Through the network, computer 1900 may be logically connected to remote computers. The networks with which computer 1900 may interact include, but are not limited to, a local area network (LAN), a wide area network (WAN), or other networks, including the cloud.

Examples herein can include subject matter such as an apparatus, an MRI system, a CT system, an optical microscopy system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting PCa progression risk, according to embodiments and examples described.

Example 1 is a non-transitory computer-readable storage device storing computer-executable instructions that when executed cause a processor to perform operations, the operations comprising: accessing a multi-parametric magnetic resonance imaging (MRI) image associated with a patient, where the image includes a region of interest (ROI) demonstrating prostate cancer (PCa) pathology, the image having a plurality of pixels, a pixel having an intensity; segmenting a tumoral region represented in the image, where segmenting the tumoral region includes defining a tumoral boundary; defining a peritumoral region based on the tumoral boundary; extracting a set of radiomic features from the image, where the set of radiomic features includes at least one radiomic feature extracted from the peritumoral region, and at least one, different radiomic feature extracted from the tumoral region; providing the set of radiomic features to a machine learning classifier trained to distinguish a first class from a second, different class based on the set of radiomic features; receiving, from the machine learning classifier, a probability that the ROI is a member of the first class, where the machine learning classifier computes the probability based on the set of radiomic features; classifying the ROI as a member of the first class or the second, different class based, at least in part, on the probability; and displaying the classification.

Example 2 comprises the subject matter of any variation of any of example(s) 1, wherein the multi-parametric MRI image is a bi-parametric MRI (bpMRI) image comprising a T2W MRI image and an apparent diffusion coefficient (ADC) map.

Example 3 comprises the subject matter of any variation of any of example(s) 1-2, where defining the peritumoral region comprises performing a dilation of the tumoral boundary, where the peritumoral region includes a plurality of annular rings.

Example 4 comprises the subject matter of any variation of any of example(s) 1-3, where performing a dilation of the tumoral boundary comprises dilating the tumoral boundary 12 mm, and where the plurality of annular rings comprises four annular rings.

Example 5 comprises the subject matter of any variation of any of example(s) 1-4, where the machine learning classifier is a quadratic discriminant analysis (QDA) classifier.

Example 6 comprises the subject matter of any variation of any of example(s) 1-5, where the first class is low risk of progression, and where the second class is high risk of progression.

Example 7 comprises the subject matter of any variation of any of example(s) 1-6, where the set of radiomic features includes an intratumoral Laws (15) feature extracted from the T2W image, an intratumoral Canny feature extracted from the T2W image, a peritumoral co-occurrence of local anisotropic gradient orientations (CoLlAGe) entropy feature extracted from the ADC map, an intratumoral Laws (11) feature extracted from the ADC image, an intratumoral Haralick (entropy) feature extracted from the ADC map, an intratumoral CoLlAGe feature extracted from the ADC map, a peritumoral Haralick (info measure 1) feature extracted from the T2W image, a peritumoral Laws (17) feature extracted from the ADC map, an intratumoral Haralick (info measure 2) feature extracted from the T2W image, and an intratumoral Haralick (info measure 2) feature extracted from the ADC map.

Example 8 comprises the subject matter of any variation of any of example(s) 1-7, where the first class is low risk of progression, and where the second class is intermediate risk of progression or high risk of progression.

Example 9 comprises the subject matter of any variation of any of example(s) 1-8, where the set of radiomic features includes an intratumoral Gabor (6 Hz, 2.0 rad) feature extracted from the T2W image, a peritumoral Gabor (6 Hz, 2.8 rad) feature extracted from the T2W image, a peritumoral Haralick (momentum sum) feature extracted from the ADC map, an intratumoral Gabor (6 Hz, 1.8 rad) feature extracted from the ADC map, a mean filter (3 pixel by 3 pixel window) response feature extracted from the peritumoral region of the T2W image, an intratumoral Gabor (2.5 Hz, 0.4 rad) feature extracted from the T2W image, an intratumoral Gabor (3 Hz, 0.4 rad) feature extracted from the T2W image, an intratumoral Gabor (3.5 Hz, 0.4 rad) feature extracted from the T2W image, an intratumoral Gabor (5 Hz, 1.6 rad) feature extracted from the ADC map, and an intratumoral Gabor (6 Hz, 1.6 rad) feature extracted from the ADC map.

Example 10 comprises the subject matter of any variation of any of example(s) 1-9, the operations further comprising preprocessing the image.

Example 11 comprises the subject matter of any variation of any of example(s) 1-10, where preprocessing the image comprises: resampling the image to a pixel size of 0.5×0.5 $mm^2$; cropping the ROI with 2 mm padding along the x axis and y axis; interpolating the image to a 3 mm slice thickness; verifying that the T2W image and ADC map represent the same three dimensional (3D) space; and correcting scanner variability using a drift correction approach.

Example 12 comprises the subject matter of any variation of any of example(s) 1-11, the operations further comprising: generating a personalized treatment plan based, at least in part, on the classification; and displaying the personalized treatment plan.

Example 13 comprises the subject matter of any variation of any of example(s) 1-12, the operations further comprising training the machine learning classifier on a multi-institutional cohort.

Example 14 comprises the subject matter of any variation of any of example(s) 1-13, the operations further comprising testing the machine learning classifier on a multi-institutional testing cohort.

Example 15 comprises an apparatus comprising: a processor; a memory configured to store a bi-parametric magnetic resonance imaging (bpMRI) image associated with a patient, where the image includes a region of interest (ROI) demonstrating prostate cancer (PCa) pathology, the bpMRI image having a plurality of pixels, a pixel having an intensity, the bpMRI image comprising a T2W MRI image and an apparent diffusion coefficient (ADC) map; an input/output (I/O) interface; a set of circuits; and an interface that connects the processor, the memory, the I/O interface, and the set of circuits, the set of circuits comprising: an image acquisition circuit configured to: access the bpMRI image; a region definition circuit configured to: segment a tumoral region represented in the bpMRI image, where segmenting the tumoral region includes defining a tumoral boundary; and define a peritumoral region based on the tumoral boundary, where the peritumoral region includes a plurality of annular rings; a radiomic feature circuit configured to: extract a first set of radiomic features from the bpMRI image, where the first set of radiomic features includes at least one radiomic feature extracted from the peritumoral region, and at least one, different radiomic feature extracted from the tumoral region; a PCa classification circuit configured to: compute a first probability that the patient associated with the ROI has a low-risk of PCa progression, or a high-risk of PCa progression based on the first set of radiomic features; generate a first classification of the patient as having low-risk of PCa progression, or a high-risk of PCa progression based, at least in part, on the probability; and a display circuit configured to display the first classification.

Example 16 comprises the subject matter of any variation of any of example(s) 15, where the set of radiomic features includes an intratumoral Laws (15) feature extracted from the T2W image, an intratumoral Canny feature extracted from the T2W image, a peritumoral co-occurrence of local anisotropic gradient orientations (CoLlAGe) entropy feature extracted from the ADC map, an intratumoral Laws (11) feature extracted from the ADC image, an intratumoral Haralick (entropy) feature extracted from the ADC map, an intratumoral CoLlAGe feature extracted from the ADC map, a peritumoral Haralick (info measure 1) feature extracted from the T2W image, a peritumoral Laws (17) feature extracted from the ADC map, an intratumoral Haralick (info measure 2) feature extracted from the T2W image, and an intratumoral Haralick (info measure 2) feature extracted from the ADC map.

Example 17 comprises the subject matter of any variation of any of example(s) 15-16, where the radiomic feature circuit is further configured to: extract a second set of radiomic features from the bpMRI image, where the second set of radiomic features includes at least one radiomic feature extracted from the peritumoral region, and at least one, different radiomic feature extracted from the tumoral region; where the PCa classification circuit is further configured to: compute a second probability that the patient associated with the ROI has a low-risk of PCa progression, or a high-risk of PCa progression or intermediate-risk of PCa progression based on the second set of radiomic features; and generate a second classification of the patient as having low-risk of PCa progression, or a high-risk or intermediate-risk of PCa progression based, at least in part, on the second probability; and where the display circuit is further configured to display the second classification.

Example 18 comprises the subject matter of any variation of any of example(s) 15-17, where the second set of radiomic features includes an intratumoral Gabor (6 Hz, 2.0 rad) feature extracted from the T2W image, a peritumoral Gabor (6 Hz, 2.8 rad) feature extracted from the T2W image, a peritumoral Haralick (momentum sum) feature extracted from the ADC map, an intratumoral Gabor (6 Hz, 1.8 rad) feature extracted from the ADC map, a mean filter (3 pixel by 3 pixel window) response feature extracted from the peritumoral region of the T2W image, an intratumoral Gabor (2.5 Hz, 0.4 rad) feature extracted from the T2W image, an intratumoral Gabor (3 Hz, 0.4 rad) feature extracted from the T2W image, an intratumoral Gabor (3.5 Hz, 0.4 rad) feature extracted from the T2W image, an intratumoral Gabor (5 Hz, 1.6 rad) feature extracted from the ADC map, and an intratumoral Gabor (6 Hz, 1.6 rad) feature extracted from the ADC map.

Example 19 comprises the subject matter of any variation of any of example(s) 15-18, where the PCa classification circuit is configured as a quadratic discriminant analysis (QDA) classifier.

Example 20 comprises the subject matter of any variation of any of example(s) 15-19, where the set of circuits further comprises: a pre-processing circuit configured to preprocess the bpMRI image by: resampling the image to a pixel size of 0.5×0.5 mm$^2$; cropping the ROI with 2 mm padding along the x axis and y axis; interpolating the image to a 3 mm slice thickness; verifying that the T2W image and ADC map represent the same three dimensional (3D) space; and correcting scanner variability using a drift correction approach.

Example 21 comprises the subject matter of any variation of any of example(s) 15-20, where the set of circuits further comprises: a PCa personalized treatment plan circuit configured to: generate a personalized treatment plan based, at least in part, on the classification; and where the display circuit is further configured to display the personalized treatment plan.

Example 22 comprises the subject matter of any variation of any of example(s) 15-21, where the set of circuits further comprises: a training and testing circuit configured to: train the PCa classification circuit on a multi-institutional cohort; and optionally test the PCa classification circuit on a multi-institutional testing cohort.

Example 23 comprises a non-transitory computer-readable storage device storing computer-executable instructions that when executed cause a processor to perform operations, the operations comprising: accessing a training dataset of a plurality of bi-parametric magnetic resonance imaging (bpMRI) images of tissue demonstrating prostate cancer (PCa), where each bpMRI image of the plurality of bpMRI images comprises an associated plurality of pixels, each pixel of the associated plurality of pixels having an associated intensity, where each bpMRI image is associated with a patient, and where a PCa progression risk for each patient is known; determining, for each radiomic feature of N radiomic features extracted from each bpMRI image, N being an integer, an associated value for that radiomic feature for each bpMRI image of the training dataset, where the N radiomic features includes at least one tumoral radiomic feature and at least one peritumoral radiomic feature; and training a quadratic discriminant analysis (QDA) classifier based on the training dataset, the associated values for each radiomic feature of the N radiographic features for each bpMRI image of the training dataset, and the known risk of PCa progression associated with each bpMRI image of the training dataset.

Example 24 comprises the subject matter of any variation of any of example(s) 23, where the N radiomic features comprise the N most distinguishing radiomic features as determined using one of a Wilcoxon rank-sum test, or a minimum redundancy maximum relevance (mRMR) feature selection technique.

Example 25 comprises a machine readable storage device that stores instructions for execution by a processor to perform any of the described operations of examples 1-24.

Example 26 comprises an apparatus comprising: a memory; and one or more processors configured to: perform any of the described operations of examples 1-24.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that when executed cause a processor to perform operations, the operations comprising:

accessing a multi-parametric magnetic resonance imaging (MRI) image associated with a patient, where the image includes a region of interest (ROI) demonstrating prostate cancer (PCa) pathology, the image having a plurality of pixels, a pixel having an intensity;

segmenting a tumoral region represented in the image, where segmenting the tumoral region includes defining a tumoral boundary;

defining a peritumoral region based on the tumoral boundary;

extracting a set of radiomic features from the image, where the set of radiomic features includes at least one radiomic feature extracted from the peritumoral region, and at least one, different radiomic feature extracted from the tumoral region;

providing the set of radiomic features to a machine learning classifier trained to distinguish a first class from a second, different class based on the set of radiomic features;

receiving, from the machine learning classifier, a probability that the ROI is a member of the first class, where the machine learning classifier computes the probability based on the set of radiomic features;

classifying the ROI as a member of the first class or the second, different class based, at least in part, on the probability; and displaying the classification, where defining the peritumoral region comprises performing a dilation of the tumoral boundary, where the peritumoral region includes a plurality of annular rings.

2. The non-transitory computer-readable storage device of claim 1, where the multi-parametric MRI image is a bi-parametric MRI (bpMRI) image comprising a T2W MRI image and an apparent diffusion coefficient (ADC) map.

3. The non-transitory computer-readable storage device of claim 1, where performing a dilation of the tumoral boundary comprises dilating the tumoral boundary 12 mm, and where the plurality of annular rings comprises four annular rings.

4. The non-transitory computer-readable storage device of claim 1, where the machine learning classifier is a quadratic discriminant analysis (QDA) classifier.

5. The non-transitory computer-readable storage device of claim 1, the operations further comprising:
generating a personalized treatment plan based, at least in part, on the classification; and
displaying the personalized treatment plan.

6. The non-transitory computer-readable storage device of claim 1, the operations further comprising training the machine learning classifier on a multi-institutional cohort.

7. The non-transitory computer-readable storage device of claim 2, where the first class is low risk of progression, and where the second class is high risk of progression.

8. The non-transitory computer-readable storage device of claim 2, where the first class is low risk of progression, and where the second class is intermediate risk of progression or high risk of progression.

9. The non-transitory computer-readable storage device of claim 2, the operations further comprising preprocessing the image.

10. The non-transitory computer-readable storage device of claim 6, the operations further comprising testing the machine learning classifier on a multi-institutional testing cohort.

11. The non-transitory computer-readable storage device of claim 7, where the set of radiomic features includes an intratumoral Laws (15) feature extracted from the T2W image, an intratumoral Canny feature extracted from the T2W image, a peritumoral co-occurrence of local anisotropic gradient orientations (CoLIAGe) entropy feature extracted from the ADC map, an intratumoral Laws (11) feature extracted from the ADC map, an intratumoral Haralick (entropy) feature extracted from the ADC map, an intratumoral CoLIAGe feature extracted from the ADC map, a peritumoral Haralick (info measure 1) feature extracted from the T2W image, a peritumoral Laws (17) feature extracted from the ADC map, an intratumoral Haralick (info measure 2) feature extracted from the T2W image, and an intratumoral Haralick (info measure 2) feature extracted from the ADC map.

12. The non-transitory computer-readable storage device of claim 8, where the set of radiomic features includes an intratumoral Gabor (6 Hz, 2.0 rad) feature extracted from the T2W image, a peritumoral Gabor (6 Hz, 2.8 rad) feature extracted from the T2W image, a peritumoral Haralick (momentum sum) feature extracted from the ADC map, an intratumoral Gabor (6 Hz, 1.8 rad) feature extracted from the ADC map a mean filter (3 pixel by 3 pixel window) response feature extracted from the peritumoral region of the T2W image, an intratumoral Gabor (2.5 Hz, 0.4 rad) feature extracted from the T2W image, an intratumoral Gabor (3 Hz, 0.4 rad) feature extracted from the T2W image, an intratumoral Gabor (3.5 Hz, 0.4 rad) feature extracted from the T2W image, an intratumoral Gabor (5 Hz, 1.6 rad) feature extracted from the ADC map, and an intratumoral Gabor (6 Hz, 1.6 rad) feature extracted from the ADC map.

13. The non-transitory computer-readable storage device of claim 9, where preprocessing the image comprises:
resampling the image to a pixel size of 0.5×0.5 mm$^2$;
cropping the ROI with 2 mm padding along the x axis and y axis;
interpolating the image to a 3 mm slice thickness;
verifying that the T2W image and ADC map represent the same three dimensional (3D) space; and
correcting scanner variability using a drift correction approach.

14. An apparatus comprising:
a processor;
a memory configured to store a bi-parametric magnetic resonance imaging (bpMRI) image associated with a patient, where the image includes a region of interest (ROI) demonstrating prostate cancer (PCa) pathology, the bpMRI image having a plurality of pixels, a pixel having an intensity, the bpMRI image comprising a T2W MRI image and an apparent diffusion coefficient (ADC) map;
an input/output (I/O) interface;
a set of circuits; and
an interface that connects the processor, the memory, the I/O interface, and the set of circuits, the set of circuits comprising:
an image acquisition circuit configured to:
access the bpMRI image;
a region definition circuit configured to:
segment a tumoral region represented in the bpMRI image, where segmenting the tumoral region includes defining a tumoral boundary; and
define a peritumoral region based on the tumoral boundary, where the peritumoral region includes a plurality of annular rings;
a radiomic feature circuit configured to:
extract a first set of radiomic features from the bpMRI image, where the first set of radiomic features includes at least one radiomic feature extracted from the peritumoral region, and at least one, different radiomic feature extracted from the tumoral region;
a PCa classification circuit configured to:
compute a first probability that the patient associated with the ROI has a low-risk of PCa progression, or a high-risk of PCa progression based on the first set of radiomic features;
generate a first classification of the patient as having low-risk of PCa progression, or a high-risk of PCa progression based, at least in part, on the probability; and
a display circuit configured to display the first classification.

15. The apparatus of claim 14, where the set of radiomic features includes an intratumoral Laws (15) feature extracted from the T2W image, an intratumoral Canny feature extracted from the T2W image, a peritumoral co-occurrence of local anisotropic gradient orientations (CoLIAGe) entropy feature extracted from the ADC map, an intratumoral Laws (11) feature extracted from the ADC image, an intratumoral Haralick (entropy) feature extracted from the ADC map, an intratumoral CoLIAGe feature extracted from the ADC map, a peritumoral Haralick (info measure 1) feature extracted from the T2W image, a peritumoral Laws (17) feature extracted from the ADC map, an intratumoral Haralick (info measure 2) feature extracted from the T2W image, and an intratumoral Haralick (info measure 2) feature extracted from the ADC map.

16. The apparatus of claim 14,
where the radiomic feature circuit is further configured to:
extract a second set of radiomic features from the bpMRI image, where the second set of radiomic features includes at least one radiomic feature extracted from the peritumoral region, and at least one, different radiomic feature extracted from the tumoral region;
where the PCa classification circuit is further configured to:

compute a second probability that the patient associated with the ROI has a low-risk of PCa progression, or a high-risk of PCa progression or intermediate-risk of PCa progression based on the second set of radiomic features; and generate a second classification of the patient as having low-risk of PCa progression, or a high-risk or intermediate-risk of PCa progression based, at least in part, on the second probability; and where the display circuit is further configured to display the second classification.

17. The apparatus of claim 14, where the PCa classification circuit is configured as a
quadratic discriminant analysis (QDA) classifier.

18. The apparatus of claim 14, where the set of circuits further comprises:
a pre-processing circuit configured to preprocess the bpMRI image by:
resampling the image to a pixel size of 0.5×0.5 mm$^2$;
cropping the ROI with 2 mm padding along the x axis and y axis;
interpolating the image to a 3 mm slice thickness;
verifying that the T2W image and ADC map represent the same three dimensional (3D) space; and
correcting scanner variability using a drift correction approach.

19. The apparatus of claim 14, where the set of circuits further comprises:
a PCa personalized treatment plan circuit configured to:
generate a personalized treatment plan based, at least in part, on the classification;
and where the display circuit is further configured to display the personalized treatment plan.

20. The apparatus of claim 14, where the set of circuits further comprises:
a training and testing circuit configured to:
train the PCa classification circuit on a multi-institutional cohort; and optionally
test the PCa classification circuit on a multi-institutional testing cohort.

21. The apparatus of claim 16, where the second set of radiomic features includes an intratumoral Gabor (6 Hz, 2.0 rad) feature extracted from the T2W image, a peritumoral Gabor (6 Hz, 2.8 rad) feature extracted from the T2W image, a peritumoral Haralick (momentum sum) feature extracted from the ADC map, an intratumoral Gabor (6 Hz, 1.8 rad) feature extracted from the ADC map, a mean filter (3 pixel by 3 pixel window) response feature extracted from the peritumoral region of the T2W image, an intratumoral Gabor (2.5 Hz, 0.4 rad) feature extracted from the T2W image, an intratumoral Gabor (3 Hz, 0.4 rad) feature extracted from the T2W image, an intratumoral Gabor (3.5 Hz, 0.4 rad) feature extracted from the T2W image, an intratumoral Gabor (5 Hz, 1.6 rad) feature extracted from the ADC map, and an intratumoral Gabor (6 Hz, 1.6 rad) feature extracted from the ADC map.

22. A non-transitory computer-readable storage device storing computer-executable instructions that when executed cause a processor to perform operations, the operations comprising:
accessing a training dataset of a plurality of bi-parametric magnetic resonance imaging (bpMRI) images of tissue demonstrating prostate cancer (PCa), where each bpMRI image of the plurality of bpMRI images comprises an associated plurality of pixels, each pixel of the associated plurality of pixels having an associated intensity, where each bpMRI image is associated with a patient, and where a PCa progression risk for each patient is known;
determining, for each radiomic feature of N radiomic features extracted from each bpMRI image, N being an integer, an associated value for that radiomic feature for each bpMRI image of the training dataset, where the N radiomic features includes at least one tumoral radiomic feature and at least one peritumoral radiomic feature; and training a quadratic discriminant analysis (QDA) classifier based on the training dataset, the associated values for each radiomic feature of the N radiographic features for each bpMRI image of the training dataset, and the known risk of PCa progression associated with each bpMRI image of the training dataset,
wherein the at least one tumoral feature is associated with a tumoral region, wherein the at least one peritumoral feature is associated with a peritumoral region defined by performing a dilation of a tumoral boundary of the tumoral region, and wherein the peritumoral region includes a plurality of annular rings.

23. The non-transitory computer-readable medium of claim 22, where the N radiomic features comprise the N most distinguishing radiomic features as determined using one of a Wilcoxon rank-sum test, or a minimum redundancy maximum relevance (mRMR) feature selection technique.

* * * * *

UNITED STATES PATENT AND TRADEMARK OFFICE
CERTIFICATE OF CORRECTION

PATENT NO. : 11,011,265 B2
APPLICATION NO. : 16/395904
DATED : May 18, 2021
INVENTOR(S) : Anant Madabhushi et al.

It is certified that error appears in the above-identified patent and that said Letters Patent is hereby corrected as shown below:

In the Specification

Column 1, Lines 18 through 26; please replace "This invention was made with government support under the grant(s) 1U24CA199374-01, R01 CA202752-01A1 R01 CA208236-01A1 R21 CA179327-01, R21 CA195152-01, R01 DK098503-02, R01 CA216579-01A1, R01 CA220581-01A1, 1 C06 RR12463-01, and VA IBX004121A awarded by the National Institutes of Health. Also awards W81XWH-15-1-0558, W81XWH-16-1-0329, and W81XWH-17-PCRP-IDA awarded by the Department of Defense. The government has certain rights in the invention." with --This invention was made with government support under the grant(s) RR012463, CA179327, CA195152, CA199374, DK098503, CA202752, CA208236, CA220581, and CA216579 awarded by the National Institutes of Health; and awards W81XWH-15-1-0558, W81XWH-16-1-0329, and W81XWH-18-1-0524 awarded by the Department of Defense; and the grant(s) IBX004121A awarded by the United States Department of Veterans Affairs. The government has certain rights in the invention.--

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*